US010369700B2

(12) United States Patent
Kuroda et al.

(10) Patent No.: US 10,369,700 B2
(45) Date of Patent: Aug. 6, 2019

(54) ROBOT ARM APPARATUS, ROBOT ARM APPARATUS CONTROL METHOD, AND PROGRAM

(71) Applicants: SONY CORPORATION, Tokyo (JP); SONY OLYMPUS MEDICAL SOLUTIONS INC., Hachioji-shi (JP)

(72) Inventors: Yohei Kuroda, Tokyo (JP); Takara Kasai, Tokyo (JP); Yasuhisa Kamikawa, Tokyo (JP); Wataru Kokubo, Tokyo (JP); Toshimitsu Tsuboi, Tokyo (JP); Tetsuharu Fukushima, Tokyo (JP); Yasuhiro Matsuda, Tokyo (JP); Atsushi Miyamoto, Kanagawa (JP); Kenji Hirose, Tokyo (JP)

(73) Assignees: SONY CORPORATION, Tokyo (JP); SONY OLYMPUS MEDICAL SOLUTIONS INC., Hachioji-shi (JP)

( * ) Notice: Subject to any disclaimer, the term of this patent is extended or adjusted under 35 U.S.C. 154(b) by 107 days.

(21) Appl. No.: 15/126,552

(22) PCT Filed: Mar. 20, 2015

(86) PCT No.: PCT/JP2015/058568
§ 371 (c)(1),
(2) Date: Sep. 15, 2016

(87) PCT Pub. No.: WO2015/146850
PCT Pub. Date: Oct. 1, 2015

(65) Prior Publication Data
US 2017/0080574 A1 Mar. 23, 2017

(30) Foreign Application Priority Data
Mar. 28, 2014 (JP) ................................. 2014-069790

(51) Int. Cl.
B25J 9/16 (2006.01)
A61B 34/35 (2016.01)
(Continued)

(52) U.S. Cl.
CPC ............. *B25J 9/1697* (2013.01); *A61B 34/30* (2016.02); *A61B 34/35* (2016.02); *A61B 34/74* (2016.02);
(Continued)

(58) Field of Classification Search
CPC ...... B25J 9/1697; B25J 9/1641; B25J 9/1651; A61B 34/35; A61B 34/74; A61B 90/361;
(Continued)

(56) References Cited

U.S. PATENT DOCUMENTS 5,436,542 A    7/1995  Petelin et al.
6,471,363 B1  10/2002  Howell et al.
(Continued)

FOREIGN PATENT DOCUMENTS

EP    2856923 A1 *  2/2013
EP    3135445 A1 *  3/2015
(Continued)

OTHER PUBLICATIONS

Extended European Search Report dated Oct. 30, 2017 in Patent Application No. 15770077.4.
(Continued)

Primary Examiner — Jaime Figueroa
(74) Attorney, Agent, or Firm — Oblon, McClelland, Maier & Neustadt, L.L.P.

(57) ABSTRACT

A robot arm apparatus according to the present disclosure includes: one or a plurality of a joint unit that joins a plurality of links constituting a multi-link structure; an acquisition unit that acquires an on-screen enlargement factor of a subject imaged by an imaging unit attached to the
(Continued)

multi-link structure; and a driving control unit that controls driving of the joint unit based on a state of the joint unit and the enlargement factor.

25 Claims, 13 Drawing Sheets

(51) Int. Cl.
    *A61B 34/00*     (2016.01)
    *A61B 34/30*     (2016.01)
    *H04N 5/225*     (2006.01)
    *A61B 90/00*     (2016.01)
    *A61B 90/50*     (2016.01)

(52) U.S. Cl.
    CPC ........... *A61B 90/361* (2016.02); *B25J 9/1641* (2013.01); *B25J 9/1651* (2013.01); *H04N 5/2251* (2013.01); *A61B 90/50* (2016.02); *A61B 2034/743* (2016.02); *A61B 2034/744* (2016.02); *A61B 2090/371* (2016.02); *G05B 2219/40613* (2013.01); *G05B 2219/41397* (2013.01)

(58) Field of Classification Search
    CPC .............. A61B 34/30; A61B 2034/743; A61B 2034/744; A61B 2090/371; A61B 90/50; H04N 5/2251; G05B 2219/41397; G05B 2219/40613
    USPC .................................................. 700/245, 259
    See application file for complete search history.

(56) References Cited

U.S. PATENT DOCUMENTS

| | | | |
|---|---|---|---|
| 6,639,623 | B2 | 10/2003 | Howell et al. |
| 6,899,442 | B2 | 5/2005 | Howell et al. |
| 8,322,468 | B2 | 12/2012 | Nagasaka |
| 8,463,433 | B2 | 6/2013 | Nagasaka |
| 8,996,170 | B2 | 3/2015 | Orita |
| 9,162,358 | B2 | 10/2015 | Geffard et al. |
| 9,699,445 | B2 * | 7/2017 | Hoffman ............ H04N 13/0468 |
| 2004/0176875 | A1 * | 9/2004 | Iribe .................... B62D 57/032 700/245 |
| 2007/0129846 | A1 * | 6/2007 | Birkenbach ............ A61B 34/70 700/245 |
| 2009/0245600 | A1 * | 10/2009 | Hoffman ............ A61B 1/00039 382/128 |
| 2009/0248036 | A1 * | 10/2009 | Hoffman ................ A61B 1/045 606/130 |
| 2010/0039506 | A1 * | 2/2010 | Sarvestani ........... A61B 90/361 348/65 |
| 2011/0208355 | A1 * | 8/2011 | Tsusaka ................ B25J 9/1664 700/246 |
| 2013/0110290 | A1 * | 5/2013 | Geffard .................. B25J 9/1679 700/258 |
| 2013/0116827 | A1 * | 5/2013 | Inazumi ................ B25J 9/1612 700/260 |
| 2013/0218005 | A1 * | 8/2013 | Desai ............... A61B 17/00234 600/424 |
| 2014/0067117 | A1 * | 3/2014 | Orita ...................... B25J 9/1641 700/250 |
| 2014/0240231 | A1 * | 8/2014 | Minnen ................... G06F 3/017 345/158 |
| 2015/0018841 | A1 * | 1/2015 | Seo ..................... A61B 19/2203 606/130 |
| 2015/0045812 | A1 * | 2/2015 | Seo ........................ A61B 34/30 606/130 |
| 2015/0077326 | A1 * | 3/2015 | Kramer ................. G06F 3/0325 345/156 |
| 2015/0148594 | A1 * | 5/2015 | Tadano .............. A61B 1/00149 600/102 |

FOREIGN PATENT DOCUMENTS

| | | |
|---|---|---|
| EP | 2 856 923 A1 | 4/2015 |
| JP | 63-229279 | 9/1988 |
| JP | 7-16239 A | 1/1995 |
| JP | 8-187246 A | 7/1996 |
| JP | 2000-312684 A | 11/2000 |
| JP | 2001-275931 A | 10/2001 |
| JP | 2003-517883 A | 6/2003 |
| JP | 2005-153119 | 6/2005 |
| JP | 3668269 B2 | 7/2005 |
| JP | 2006-167820 A | 6/2006 |
| JP | 2009-28851 A | 2/2009 |
| JP | 2009-78308 A | 4/2009 |
| JP | 2009-95959 A | 5/2009 |
| JP | 2010-188471 A | 9/2010 |
| JP | 2010-228064 A | 10/2010 |
| JP | 2011-209099 A | 10/2011 |
| JP | 2012-81568 A | 4/2012 |
| JP | 2013-529559 A | 7/2013 |
| JP | 2014-46417 A | 3/2014 |
| WO | WO 2012/001057 A1 | 1/2012 |
| WO | WO 2013/179693 A1 | 12/2013 |

OTHER PUBLICATIONS

International Search Report dated Jun. 23, 2015 in PCT/JP2015/058568 Filed Mar. 20, 2015.
Combined Office Action and Search Report dated Jul. 4, 2018 in Chinese Patent Application No. 201580015467.6 With unedited computer generated English translation, 14 pages.
Office Action issued in corresponding JP application 2016-510305 dated Dec. 18, 2018.
Office Action dated Mar. 31, 2019 in corresponding JP application 2016-510305.

* cited by examiner

ROBOT ARM APPARATUS, ROBOT ARM APPARATUS CONTROL METHOD, AND PROGRAM

TECHNICAL FIELD

The present disclosure relates to a robot arm apparatus, a robot arm apparatus control method, and a program.

BACKGROUND ART

Recently, in industrial fields, robot apparatuses are being used widely to perform work more accurately and more quickly. Some robot apparatuses are made of a multi-link structure in which multiple links are joined to each other by multiple joint units, and by controlling rotational driving in the multiple joint units, the driving of the robot apparatus as a whole is controlled.

Here, position control and force control are known as control methods of the robot apparatus and each of the joint units. In position control, for example, a command value such as an angle is provided to an actuator of a joint unit, and driving of the joint unit is controlled according to the command value. Meanwhile, in force control, a target value of force applied to a task target by a whole robot apparatus is given, and driving of a joint unit (for example, torque generated by the joint unit) is controlled such that the force indicated by the target value is implemented.

Generally, most robot apparatuses are driven by position control since it is convenient to control and a system configuration is simple. However, position control is commonly called "hard control" since cannot easily deal with external force flexibly, and position control is not suitable for a robot apparatus performing a task (purpose of motion) while performing physical interaction (for example, physical interaction with a person) with various external worlds. Meanwhile, force control has a complicated system configuration, but can implement "soft control" of a power order, and thus force control is a control method suitable, particularly, for a robot apparatus performing physical interaction with a person and a control method having excellent usability.

For example, with regard to an example of a robot apparatus applying force control, Patent Literature 1 discloses a robot apparatus that includes a movement mechanism configured with 2 wheels and an arm unit configured with a plurality of joint units, and performs control such that the wheels and the joint units are driven in a cooperative manner as a whole (performs whole body cooperative control).

In addition, with force control, there is demand to detect more accurately the torque in each joint unit of the robot apparatus (including the generated torque generated by the joint unit and the external torque imparted to the joint unit externally), and perform feedback control and/or feed-forward control. For example, Patent Literature 2 discloses a torque sensor that, by including a split structure (decoupled structure), realize accurate torque detection with the influence of vibration decreased as much as possible.

Also, Patent Literature 3 below describes a technology that uses a surgical microscope adopting a structure with a balanced center of gravity to thereby enable operation with a light operating force.

CITATION LIST

Patent Literature

Patent Literature 1: JP 2010-188471A
Patent Literature 2: JP 2011-209099A
Patent Literature 3: JP 7-16239A

SUMMARY OF INVENTION

Technical Problem

In recent years, in the medical field, attempts to use a balance arm (also referred to as support arm) in which various medical units (front edge units) are installed at a front edge of an arm unit when various medical procedures (for example, surgery or an examination) are performed have been made. However, with a typical balance arm, since the arm is balanced, the arm will move in response to a light force, making it to operate with slight amounts of movement, and also making it difficult to ensure freedom of imaging, such as imaging from a variety of directions in a state in which the imaging site is locked to a certain site on the patient's body, for example.

In light of the above circumstances, as a device to replace a balance arm, there also proposed a medical robot arm apparatus whose driving is controlled by position control in order. However, in order to more efficiently perform a medical procedure and reduce a burden on a user, high operability enabling more intuitive control of a position or posture of an arm unit and a front edge unit by a user is necessary for driving control of a robot arm apparatus. In a robot arm apparatus in which driving is controlled by position control, it is difficult to meet such a user demand.

Given circumstances like the above, it is desirable to realize a robot arm apparatus enabling optimal operation according to user demand.

Solution to Problem

According to the present disclosure, there is provided a robot arm apparatus including: one or a plurality of a joint unit that joins a plurality of links constituting a multi-link structure; an acquisition unit that acquires an on-screen enlargement factor of a subject imaged by an imaging unit attached to the multi-link structure; and a driving control unit that controls driving of the joint unit based on a state of the joint unit and the enlargement factor.

According to the present disclosure, there is provided a program causing a computer to function as: means for detecting a state of one or a plurality of a joint unit that joins a plurality of links constituting a multi-link structure; means for acquiring an on-screen enlargement factor of a subject imaged by an imaging unit attached to the multi-link structure; and means for controlling driving of the joint unit based on a state of the joint unit and the enlargement factor.

According to the present disclosure, there is provided a robot arm apparatus including: one or a plurality of a joint unit that joins a plurality of links constituting a multi-link structure; and a driving control unit that controls a viscosity of driving of the joint unit based on a state of the joint unit.

Advantageous Effects of Invention

According to the present disclosure, it is possible to realize a robot arm apparatus enabling optimal operation according to an image captured by an imaging unit.

DESCRIPTION OF EMBODIMENT(S)

Figure 1:
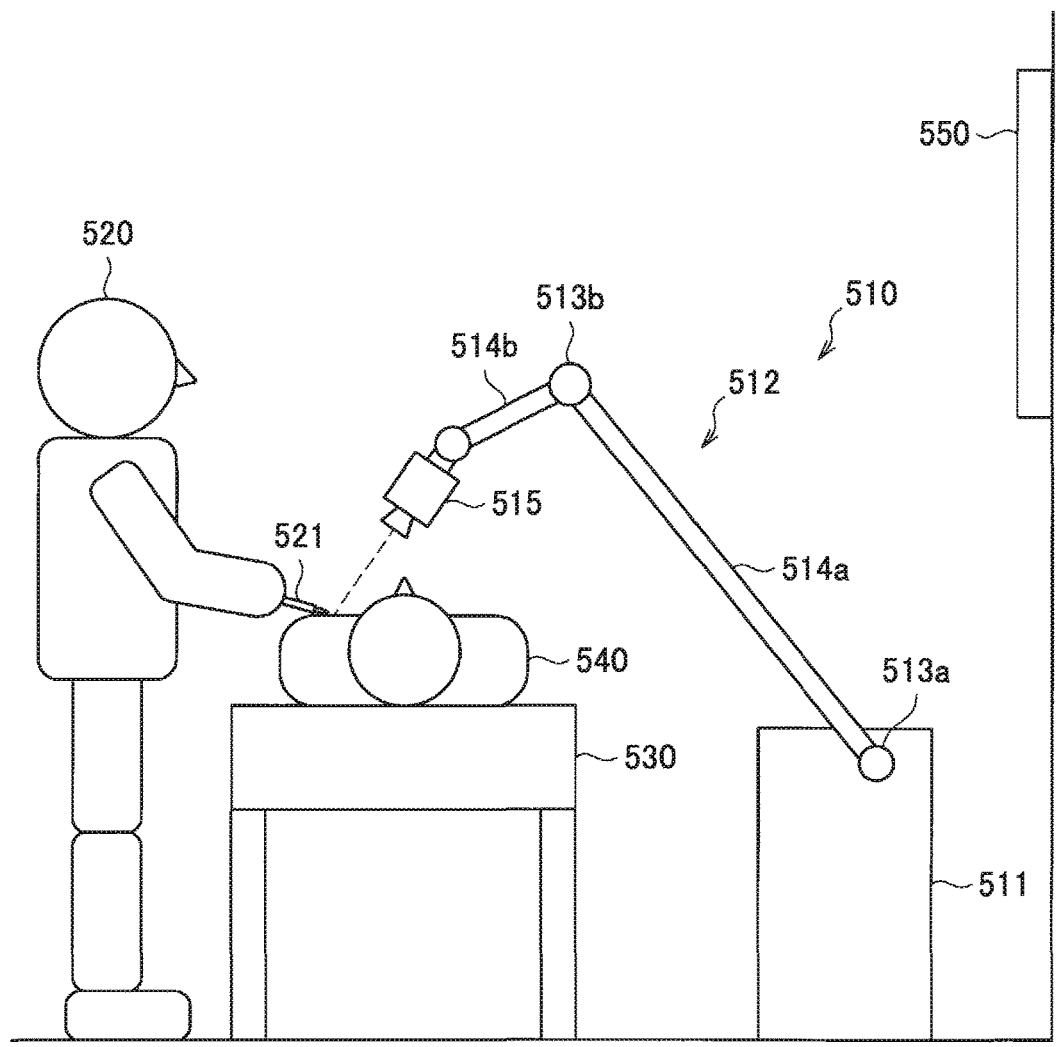
FIG. 1 is an explanatory diagram for describing an application example of using a robot arm apparatus according to an embodiment of the present disclosure for a medical purpose.

Hereinafter, (a) preferred embodiment(s) of the present disclosure will be described in detail with reference to the appended drawings. In this specification and the drawings, elements that have substantially the same function and structure are denoted with the same reference signs, and repeated explanation is omitted.

The description will proceed in the following order.
1. Review of medical robot arm apparatus
2. Embodiment of present disclosure
2-1. External appearance of robot arm apparatus
2-2. Generalized inverse dynamics
2-2-1. Virtual force calculating process
2-2-2. Actual force calculating process
2-3. Ideal joint control
2-4. Configuration of robot arm control system
2-5. Specific example of purpose of motion
3. Control according to zoom factor
4. Processing procedure of robot arm control method
5. Operation matching on-screen directions
6. Hardware configuration
7. Conclusion <1. Review of Medical Robot Arm Apparatus>

First, to further elucidate the present disclosure, the background leading up to the inventors' conception of the present disclosure will be described. For example, a method is proposed in which a unit having any of various imaging functions, such as a microscope, an endoscope, or an imaging unit (camera), is provided as a front edge unit on the front edge of an arm unit of a balance arm, and the practitioner (user) performs various medical procedures while observing an image of an affected area captured by the front edge unit. However, the balance arm has to be equipped with a counter balance weight (also called a counter weight or a balancer) for maintaining balance of force when the arm unit is moved and thus a device size tends to increase. A device used in a medical procedure has to be small in size since it is necessary to secure a task space for the medical procedure, but it is difficult to meet such a demand in general balance arms being proposed. Further, in the balance arm, only some driving of the arm unit, for example, only biaxial driving for moving the front edge unit on a (two-dimensional) plane is electric driving, and manual positioning by the practitioner or a medical staff therearound is necessary for movement of the arm unit and the front edge unit. Consequently, with a typical balance arm, it is difficult to ensure consistency during imaging (such as the positioning accuracy and vibration damping of the front edge unit, for example), such as imaging from a variety of directions in a state in which the imaging site is locked to a certain site on the patient's body, for example. In addition, if an imaging unit such as a camera is mounted to the front edge of a robot arm apparatus, in some cases a subject image captured by the imaging unit is displayed, and the operator operates the robot arm apparatus while checking the captured subject image. Additionally, if the imaging unit includes a zoom function, the degree of minor adjustment of the robot arm by the operator is different between the case of increasing the imaging magnification of the subject and the case of decreasing the imaging magnification. Consequently, when the imaging magnification is increased, usability enabling fine-grained operation by the operator is demanded. In light of such circumstances, in the present embodiment, a robot arm apparatus enabling optimal operation according to an image captured by an imaging unit is realized.

FIG. 1 will be referenced to describe an application example for the case of a robot arm apparatus according to an embodiment of the present disclosure being used for medical use. FIG. 1 is an explanatory diagram for describing an application example for the case of a robot arm apparatus according to an embodiment of the present disclosure being used for medical use.

FIG. 1 schematically illustrates an exemplary medical procedure using the robot arm apparatus according to the present embodiment. Specifically, FIG. 1 illustrates an example in which a doctor serving as a practitioner (user) 520 performs surgery on a medical procedure target (patient) 540 on a medical procedure table 530, for example, using surgical instruments 521 such as a scalpel, tweezers, and forceps. In the following description, the medical procedure refers to a general concept including various kinds of medical treatments that the doctor serving as the user 520 performs on the patient of the medical procedure target 540 such as surgery or an examination. The example of FIG. 1 illustrates surgery as an example of the medical procedure, but the medical procedure using a robot arm apparatus 510 is not limited to surgery and may be various kinds of other medical procedures such as an examination using an endoscope.

The robot arm apparatus 510 according to the present embodiment is installed at the side of the medical procedure table 530. The robot arm apparatus 510 includes a base unit 511 serving as a base and an arm unit 512 extending from the base unit 511. The arm unit 512 includes a plurality of joint units 513a, 513b, 513c, a plurality of links 514a and 514b connected by the joint units 513a and 513b, and an imaging unit 515 installed at the front edge of the arm unit 512. In the example illustrated in FIG. 1, for the sake of simplification, the arm unit 512 includes the 3 joint units 513a to 513c and the 2 links 514a and 514b, but practically, for example, the number and the shape of the joint units 513a to 513c and the links 514a and 514b and a direction of the driving shaft of the joint units 513a to 513c may be appropriately set to express a desired degree of freedom in view of a degree of freedom of the position and posture of the arm unit 512 and the imaging unit 515, The joint units 513a to 513c have a function of connecting the links 514a and 514b to be rotatable, and as the joint units 513a to 513c are rotationally driven, driving of the arm unit 512 is controlled. Here, in the following description, the position of each component of the robot arm apparatus 510 is the position (coordinates) in a space specified for driving control, and the posture of each component is a direction (angle) to an arbitrary axis in a space specified for driving control. Further, in the following description, driving (or driving control) of the arm unit 512 refers to changing (controlling a change of) the position and posture of each component of the arm unit 512 by performing driving (or driving control) of the joint units 513a to 513c and driving (or driving control) of the joint units 513a to 513c.

Various kinds of medical apparatuses are connected to the front edge of the arm unit 512 as the front edge unit. In the example illustrated in FIG. 1, the imaging unit 515 is installed at the front edge of the arm unit 512 as an exemplary front edge unit. The imaging unit 515 is a unit that acquires an image (a photographed image) of a photographing target and is, for example, a camera capable of capturing a moving image or a still image. As illustrated in FIG. 1, the posture or the position of the arm unit 512 and the imaging unit 515 is controlled by the robot arm apparatus 510 such that the imaging unit 515 installed at the front edge of the arm unit 512 photographs a state of a medical procedure part of the medical procedure target 540. The front edge unit installed at the front edge of the arm unit 512 is not limited to the imaging unit 515 and may be various kinds of medical apparatuses. For example, the medical apparatus includes various kinds of units used when the medical procedure is performed such as an endoscope, a microscope, a unit having an imaging function such as the imaging unit 515, various kinds of medical procedure instruments, and an examination apparatus. As described above, the robot arm apparatus 510 according to the present embodiment is a medical robot arm apparatus equipped with a medical apparatus. Further, a stereo camera having two imaging units (camera units) may be installed at the front edge of the arm unit 512, and may perform photography so that an imaging target is displayed as a three dimensional (3D) image.

Further, a display device 550 such as a monitor or a display is installed at a position facing the user 520. The captured image of the medical procedure part captured by the imaging unit 515 is displayed on a display screen of the display device 550. The user 520 performs various kinds of treatments while viewing the captured image of the medical procedure part displayed on the display screen of the display device 550.

As described above, in the present embodiment, in the medical field, a technique of performing surgery while photographing the medical procedure part through the robot arm apparatus 510 is proposed. Here, in various kinds of medical procedures including surgery, it is necessary to reduce fatigue or a burden on the user 520 and the patient 540 by performing the medical procedure efficiently. In order to satisfy such a demand, in the robot arm apparatus 510, for example, the following capabilities are considered desirable.

First, as a first point, the robot arm apparatus 510 should secure a task space for surgery. If the arm unit 512 or the imaging unit 515 hinders a field of vision of the practitioner or impedes motion of a hand performing a treatment while the user 520 is performing various kinds of treatments on the medical procedure target 540, the efficiency of surgery is lowered. Further, in FIG. 1, although not illustrated, in an actual surgical scene, for example, a plurality of other doctors and/or nurses performing various support tasks of handing an instrument to the user 520 or checking various kinds of vital signs of the patient 540 are commonly around the user 520 and the patient 540, and there are other devices for performing the support tasks, and thus a surgical environment is complicated. Thus, a small size is desirable in the robot arm apparatus 510.

Next, as a second point, the robot arm apparatus 510 should have high operability for moving the imaging unit 515. For example, the user 520 may desire to observe the same medical procedure part at various positions and angles while performing a treatment on the medical procedure part according to a surgical part or surgical content. In order to change an angle at which the medical procedure part is observed, it is necessary to change an angle of the imaging unit 515 with respect to the medical procedure part, but at this time, it is more desirable that only a photographing angle be changed in a state in which the photographing direction of the imaging unit 515 is fixed to the medical procedure part (that is, while photographing the same part). Thus, for example, the robot arm apparatus 510 should have operability of a high degree of freedom such as a turning movement pivot movement) in which the imaging unit 515 moves within a surface of a cone having the medical procedure part as an apex, and an axis of the cone is used as a pivot axis in the state in which the photographing direction of the imaging unit 515 is fixed to the medical procedure part. Since the photographing direction of the imaging unit 515 is fixed to a certain medical procedure part, the pivot movement is also called point lock movement.

Further, in order to change the position and the angle of the imaging unit 515, for example, a method in which the user 520 manually moves the arm unit 512 to move the imaging unit 515 to a desired position and at a desired angle is considered. Thus, it is desirable that there be operability enabling movement of the imaging unit 515, the pivot movement, or the like to be easily performed even with one hand.

Further, there may be a demand from the user 520 to move a photographing center of a captured image captured by the imaging unit 515 from a part on which a treatment is being performed to another part (for example, a part on which a next treatment will be performed) while performing a treatment with both hands during surgery. Thus, various driving methods of the arm unit 512 are necessary such as a method of controlling driving of the arm unit 512 by an operation input from an input unit such as a pedal as well as a method of controlling driving of the arm unit 512 by a manual motion when it is desired to change the position and posture of the imaging unit 515.

As described above as the capability of the second point, the robot arm apparatus 510 should have high operability enabling easy movement, for example, by the pivot movement or the manual motion and satisfying intuition or a desire of the user 520.

Lastly, as a third point, the robot arm apparatus 510 should have stability in the driving control of the arm unit 512. The stability in the driving control of the arm unit 512 may be stability in the position and posture of the front edge unit when the arm unit 512 is driven. The stability in the driving control of the arm unit 512 also includes smooth movement and suppression of vibration (vibration suppression) of the front edge unit when the arm unit 512 is driven. For example, when the front edge unit is the imaging unit 515 as in the example illustrated in FIG. 1, if the position or the posture of the imaging unit 515 is unstable, the captured image displayed on the display screen of the display device 550 is unstable, and the user may have a feeling of discomfort. Particularly, when the robot arm apparatus 510 is used for surgery, a use method in which a stereo camera including two imaging units (camera units) is installed as the front edge unit, and a 3D image generated based on photographed images obtained by the stereo camera is displayed can be assumed. As described above, when the 3D image is displayed, if the position or the posture of the stereo camera is unstable, the user is likely to experience 3D sickness. Further, an observation range photographed by the imaging unit 515 may be enlarged up to about φ15 mm depending on a surgical part or surgical content. When the imaging unit 515 enlarges and photographs a narrow range as described above, slight vibration of the imaging unit 515 is shown as a large shake or deviation of an imaged image. Thus, high positioning accuracy with a permissible range of about 1 mm is necessary for driving control of the arm unit 512 and the imaging unit 515. As described above, high-accuracy responsiveness and high positioning accuracy are necessary in driving control of the arm unit 512.

The inventors have reviewed existing general balance arms and robot arm apparatuses based on position control in terms of the above-mentioned 3 capabilities.

First, with regard to securing the task space for the surgery of the first point, in the general balance arm, a counter balance weight (also called a counter weight or a balancer) for maintaining balance of force when the arm unit is moved is installed inside the base unit or the like, and thus it is difficult to reduce the size of the balance arm apparatus, and it is difficult to say that the corresponding capability is fulfilled.

Further, with regard to the high operability of the second point, in the general balance arm, only some driving of the arm unit, for example, only biaxial driving for moving the imaging unit on a (two-dimensional) plane is electric driving, and manual positioning is necessary for movement of the arm unit and the imaging unit, and thus it is difficult to say that high operability can be implemented. Further, in the general robot arm apparatus based on the position control, since it is difficult to flexibly deal with external force by the position control used for driving control of the arm unit, that is, control of the position and posture of the imaging unit, the position control is commonly called "hard control" and is not suitable of implementing desired operability satisfying the user's intuition.

Further, with regard to stability in driving control of the arm unit of the third point, the joint unit of the arm unit generally has factors that are not easily modelized such as friction, inertia, and the like. In the general balance arm or the robot arm apparatus based on the position control, the factors serve as a disturbance in the driving control of the joint unit, and even when a theoretically appropriate control value (for example, a current value applied to a motor of the joint unit) is given, there are cases in which desired driving (for example, rotation at a desired angle in the motor of the joint unit) is not implemented, and it is difficult to implement high stability necessary for driving control of the arm unit.

As described above, the inventors have reviewed robot arm apparatuses being used for medical purposes and learned that there is a demand for the capabilities of the above-mentioned three points with regard to the robot arm apparatus. However, it is difficult for the general balance arm or the robot arm apparatus based on the position control to easily fulfill such capabilities. The inventors have developed a robot arm apparatus, a robot arm control system, a robot arm control method, and a program according to the present disclosure as a result of reviewing configurations satisfying the capabilities of the three points. Hereinafter, preferable embodiments of the configuration developed by the inventors will be described in detail.

<2. Embodiment of Present Disclosure>

A robot arm control system according to an embodiment of the present disclosure will be described below. In the robot arm control system according to the present embodiment, driving of a plurality of joint units installed in the robot arm apparatus is controlled by whole body cooperative control using generalized inverse dynamics. Further, ideal joint control of implementing an ideal response to a command value by correcting influence of a disturbance is applied to driving control of the joint unit.

In the following description of the present embodiment, an external appearance of the robot arm apparatus according to the present embodiment and a schematic configuration of the robot arm apparatus will be first described in [2-1. External appearance of robot arm apparatus]. Then, an overview of the generalized inverse dynamics and the ideal joint control used for control of the robot arm apparatus according to the present embodiment will be described in [2-2. Generalized inverse dynamics] and [2-3. Ideal joint control]. Then, a configuration of a system for controlling the robot arm apparatus according to the present embodiment will be described with reference to a functional block diagram in [2-4. Configuration of robot arm control system]. Lastly, a specific example of the whole body cooperative control using the generalized inverse dynamics in the robot arm apparatus according to the present embodiment will be described in [2-5. Specific example of purpose of motion].

Further, the following description will proceed with an example in which a front edge unit of an arm unit of a robot arm apparatus according to an embodiment of the present disclosure is an imaging unit, and a medical procedure part is photographed by the imaging unit during surgery as illustrated in FIG. 1 as an embodiment of the present disclosure, but the present embodiment is not limited to this example. The robot arm control system according to the present embodiment can be applied even when a robot arm apparatus including a different front edge unit is used for another purpose.

[2-1. External Appearance of Robot Arm Apparatus]

Figure 2:
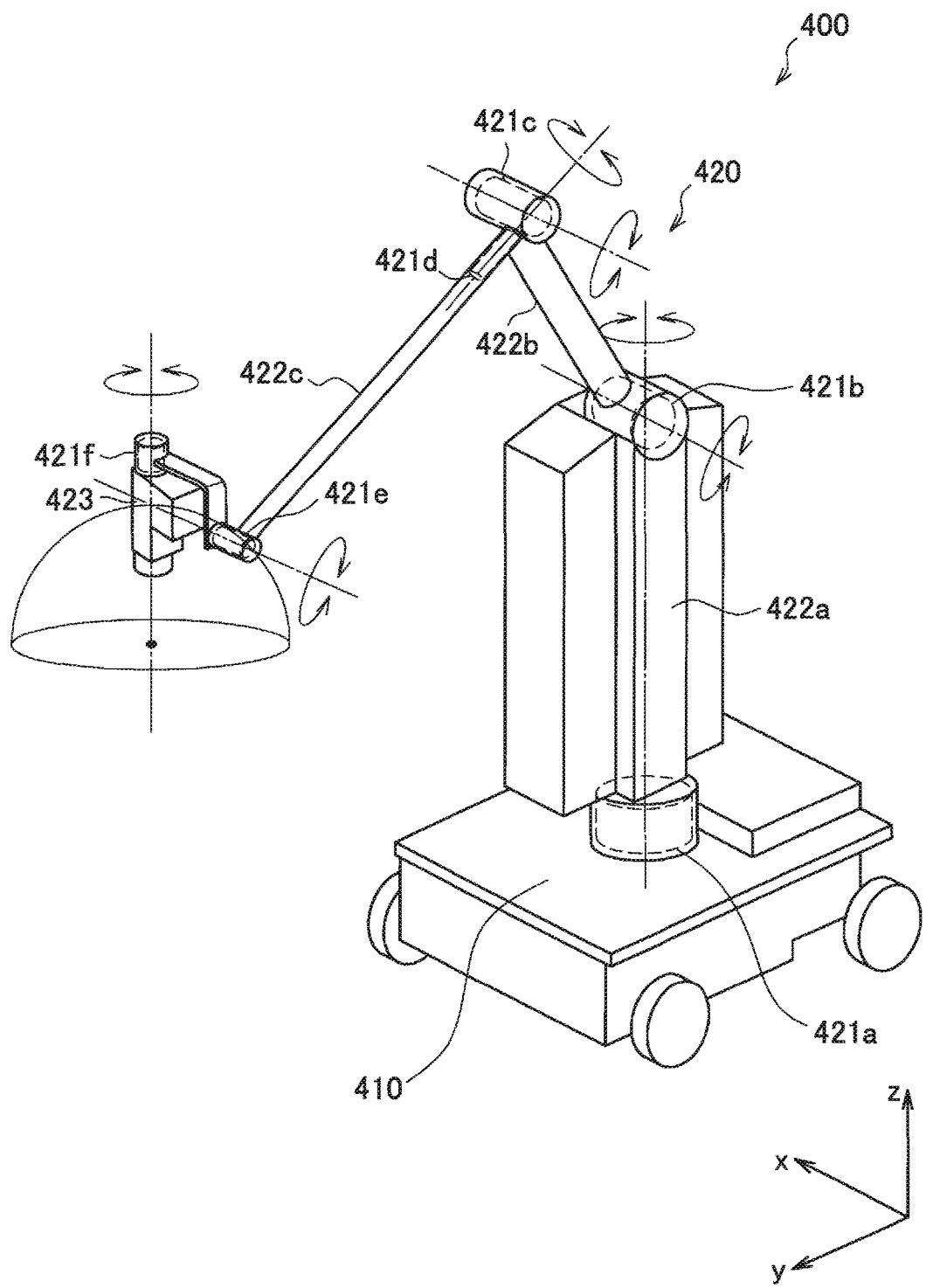
FIG. 2 is a schematic diagram illustrating an external appearance of a robot arm apparatus according to an embodiment of the present disclosure.

First, a schematic configuration of a robot arm apparatus according to an embodiment of the present disclosure will be described with reference to FIG. 2. FIG. 2 is a schematic diagram illustrating an external appearance of a robot arm apparatus according to an embodiment of the present disclosure.

Referring to FIG. 2, a robot arm apparatus 400 according to the present embodiment includes a base unit 410 and an arm unit 420. The base unit 410 serves as the base of the robot arm apparatus 400, and the arm unit 420 extends from the base unit 410. Although not illustrated in FIG. 2, a control unit that controls the robot arm apparatus 400 in an integrated manner may be installed in the base unit 410, and driving of the arm unit 420 may be controlled by the control unit. For example, the control unit is configured with various kinds of signal processing circuits such as a central processing unit (CPU) or a digital signal processor (DSP).

The arm unit 420 includes a plurality of joint units 421a to 421f, a plurality of links 422a to 422c that are connected with one another by the joint units 421a to 421f, and an imaging unit 423 installed at the front edge of the arm unit 420.

The links 422a to 422c are rod-like members, one end of the link 422a is connected with the base unit 410 through the joint unit 421a, the other end of the link 422a is connected with one end of the link 422b through the joint unit 421b, and the other end of the link 422b is connected with one end of the link 422c through the joint units 421c and 421d. Further, the imaging unit 423 is connected to the front edge of the arm unit 420, that is, the other end of the link 422c through the joint units 421e and 421f. As described above, the arm shape extending from the base unit 410 is configured such that the base unit 410 serves as a support point, and the ends of the plurality of links 422a to 422c are connected with one another through the joint units 421a to 421f.

The imaging unit 423 is a unit that acquires an image of a photographing target, and is, for example, a camera that captures a moving image, a still image. The driving of the arm unit 420 is controlled such that the position and posture of the imaging unit 423 are controlled. In the present embodiment, for example, the imaging unit 423 photographs some regions of the body of the patient serving as the medical procedure part. Here, the front edge unit installed at the front edge of the arm unit 420 is not limited to the imaging unit 423, and various kinds of medical apparatuses may be connected to the front edge of the arm unit 420 as the front edge unit. As described above, the robot arm apparatus 400 according to the present embodiment is a medical robot arm apparatus equipped with a medical apparatus.

Here, the description of the robot arm apparatus 400 will proceed with coordinate axes defined as illustrated in FIG. 2. Further, a vertical direction, a longitudinal direction, and a horizontal direction are defined according to the coordinate axes. In other words, a vertical direction with respect to the base unit 410 installed on the floor is defined as a z axis direction and a vertical direction. Further, a direction along which the arm unit 420 extends from the base unit 410 as a direction orthogonal to the z axis (that is, a direction in which the imaging unit 423 is positioned with respect to the base unit 410) is defined as a y axis direction and a longitudinal direction. Furthermore, a direction that is orthogonal to the y axis and the z axis is an x axis direction and a horizontal direction.

The joint units 421a to 421f connect the links 422a to 422c to be rotatable. Each of the joint units 421a to 421f includes a rotation mechanism that includes an actuator and is rotationally driven on a certain rotary axis according to driving of the actuator. By controlling rotary driving in each of the joint units 421a to 421f, for example, it is possible to control driving of the arm unit 420 to extend or shorten (fold) the arm unit 420. Here, driving of the joint units 421a to 421f is controlled by the whole body cooperative control which will be described in [2-2. Generalized inverse dynamics] and the ideal joint control which will be described in [2-3. Ideal joint control]. Further, as described above, since the joint units 421a to 421f according to the present embodiment include the rotation mechanism, in the following description, driving control of the joint units 421a to 421f specifically means controlling a rotational angle and/or generated torque (torque generated by the joint units 421a to 421f) of the joint units 421a to 421f.

The robot arm apparatus 400 according to the present embodiment includes the 6 joint units 421a to 421f, and implements 6 degrees of freedom with regard to driving of the arm unit 420. Specifically, as illustrated in FIG. 2, the joint units 421a, 421d, and 421f are installed such that the long axis directions of the links 422a to 422c connected thereto and the photographing direction of the imaging unit 473 connected thereto are set as the rotary axis direction, and the joint units 421b, 421c, and 421e are installed such that an x axis direction serving as a direction in which connection angles of the links 422a to 422c and the imaging unit 473 connected thereto are changed within a y-z plane (a plane specified by the y axis and the z axis) is set as the rotary axis direction. As described above, in the present embodiment, the joint units 421a, 421d, and 421f have a function of performing yawing, and the joint units 421b, 421c, and 421e have a function of performing pitching.

As the above-described configuration of the arm unit 420 is provided, the robot arm apparatus 400 according to the present embodiment can implement the 6 degrees of freedom on driving of the arm unit 420, and thus can freely move the imaging unit 423 within a movable range of the arm unit 420. FIG. 2 illustrates a hemisphere as an exemplary movable range of the imaging unit 423. When the central point of the hemisphere is the photographing center of the medical procedure part photographed by the imaging unit 423, the medical procedure part can be photographed at various angles by moving the imaging unit 423 on the spherical surface of the hemisphere in a state in which the photographing center of the imaging unit 423 is fixed to the central point of the hemisphere.

A configuration of the joint units 421a to 421f illustrated in FIG. 2 will be described herein in further detail with reference to FIG. 3. Further, a configuration of an actuator serving as a component mainly related to the rotary driving of the joint units 421a to 421f among the components of the joint units 421a to 421f will be described herein with reference to FIG. 3.

Figure 3:
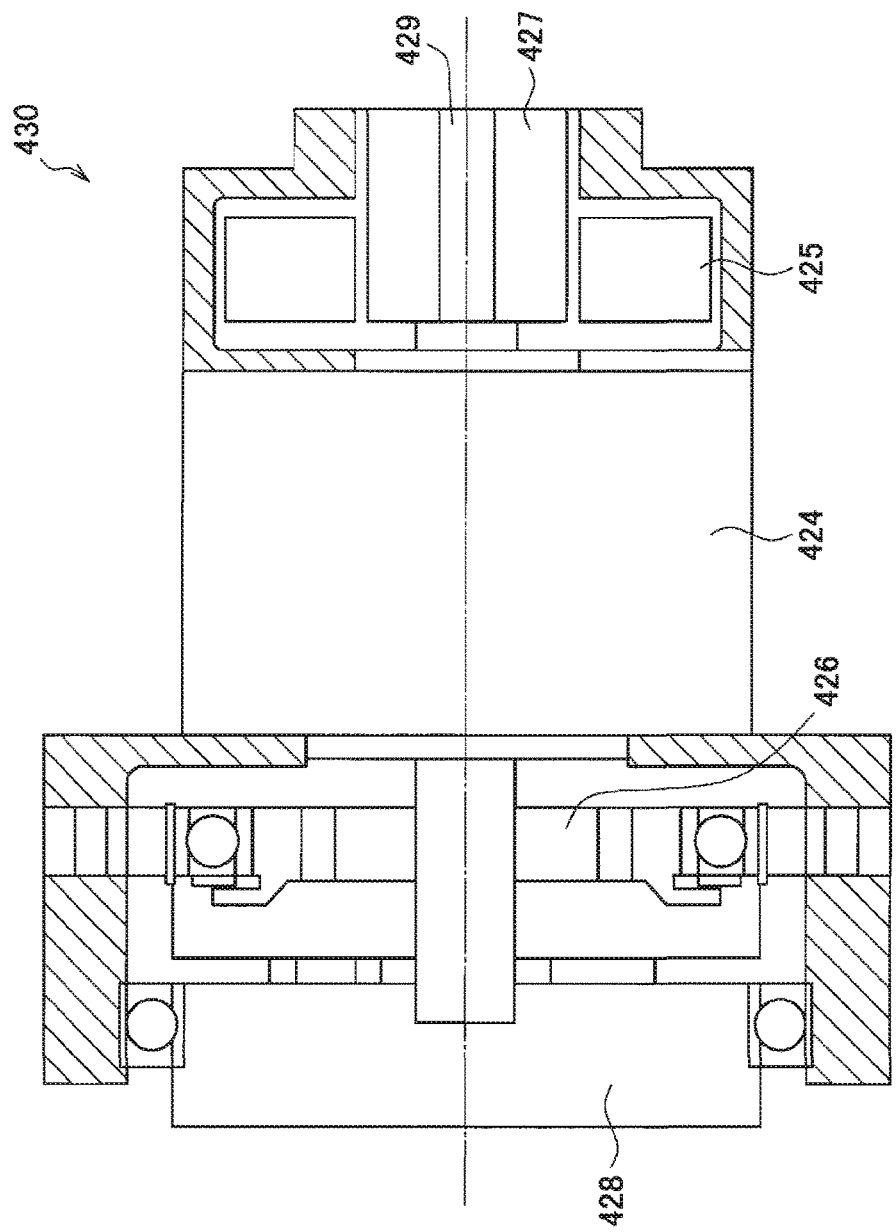
FIG. 3 is a cross-sectional diagram schematically illustrating a state in which an actuator of a joint unit according to an embodiment of the present disclosure is cut along a cross section passing through a rotary axis.

FIG. 3 is a cross-sectional diagram schematically illustrating a state in which an actuator of each of the joint units 421a to 421f according to an embodiment of the present disclosure is cut along a cross section passing through the rotary axis. FIG. 3 illustrates an actuator among the components of the joint units 421a to 421f, but the joint units 421a to 421f may have any other component. For example, the joint units 421a to 421f have various kinds of components necessary for driving of the arm unit 420 such as a control unit for controlling driving of the actuator and a support member for connecting and supporting the links 422a to 422c and the imaging unit 423 in addition to the components illustrated in FIG. 3. Further, in the above description and the following description, driving of the joint unit of the arm unit may mean driving of the actuator in the joint unit.

As described above, in the present embodiment, driving of the joint units 421a to 421f is controlled by the ideal joint control which will be described later in [2-3. Ideal joint control]. Thus, the actuator of the joint units 421a to 421f illustrated in FIG. 3 is configured to perform driving corresponding to the ideal joint control. Specifically, the actuator of the joint units 421a to 421f is configured to be able to adjust the rotational angles and torque associated with the rotary driving in the joint units 421a to 421f. Further, the actuator of the joint units 421a to 421f is configured to be able to arbitrarily adjust a viscous drag coefficient on a rotary motion. For example, it is possible to implement a state in which rotation is easily performed (that is, the arm unit 420 is easily moved by a manual motion) by force applied from the outside or a state in which rotation is not easily performed (that is, the arm unit 420 is not easily moved by a manual motion) by force applied from the outside.

Referring to FIG. 3, an actuator 430 of the joint units 421a to 421f according to the present embodiment includes a motor 424, a motor driver 425, a reduction gear 426, an encoder 427, a torque sensor 428, and a driving shaft 429. As illustrated in FIG. 3, the encoder 427, the motor 424, the reduction gear 426, and the torque sensor 428 are connected to the driving shaft 429 in series in the described order.

The motor 424 is a prime mover in the actuator 430, and causes the driving shaft 429 to rotate about its axis. For example, the motor 424 is an electric motor such as a brushless DC motor. In the present embodiment, as the motor 424 is supplied with an electric current, the rotary driving is controlled.

The motor driver 425 is a driver circuit (a driver integrated circuit (IC)) for supplying an electric current to the motor 424 and rotationally driving the motor 424, and can control the number of revolutions of the motor 424 by adjusting an amount of electric current supplied to the motor 424. Further, the motor driver 425 can adjust the viscous drag coefficient on the rotary motion of the actuator 430 by adjusting an amount of electric current supplied to the motor 424.

The reduction gear 426 is connected to the driving shaft 429, and generates rotary driving force (that is, torque) having a certain value by reducing the rotation speed of the driving shaft 429 generated by the motor 424 at a certain reduction ratio. A high-performance reduction gear of a backlashless type is used as the reduction gear 426. For example, the reduction gear 426 may be a Harmonic Drive (a registered trademark). The torque generated by the reduction gear 426 is transferred to an output member (not illustrated) (for example, a connection member of the links 422a to 422c, the imaging unit 423, or the like) at a subsequent stage through the torque sensor 428 connected to an output shaft of the reduction gear 426.

The encoder 427 is connected to the driving shaft 429, and detects the number of revolutions of the driving shaft 429. It is possible to obtain information such as the rotational angle, the rotational angular velocity, and the rotational angular acceleration of the joint units 421a to 421f based on a relation between the number of revolutions of the driving shaft 429 detected by the encoder and the reduction ratio of the reduction gear 426.

The torque sensor 428 is connected to the output shaft of the reduction gear 426, and detects the torque generated by the reduction gear 426, that is, the torque output by the actuator 430. In the following description, the torque output by the actuator 430 is also referred to simply as "generated torque."

As described above, the actuator 430 can adjust the number of revolutions of the motor 424 by adjusting an amount of electric current supplied to the motor 424. Here, the reduction ratio of the reduction gear 426 may be appropriately set according to the purpose of the robot arm apparatus 400. Thus, the generated torque can be controlled by appropriately adjusting the number of revolutions of the motor 424 according to the reduction ratio of the reduction gear 426. Further, in the actuator 430, it is possible to obtain information such as the rotational angle, the rotational angular velocity, and the rotational angular acceleration of the joint units 421a to 421f based on the number of revolutions of the driving shaft 429 detected by the encoder 427, and it is possible to detect the generated torque in the joint units 421a to 421f through the torque sensor 428.

Further, the torque sensor 428 can detect external torque applied from the outside as well as the generated torque generated by the actuator 430. Thus, as the motor driver 425 adjusts an amount of electric current supplied to the motor 424 based on the external torque detected by the torque sensor 428, it is possible to adjust the viscous drag coefficient on the rotary motion and implement, for example, the state in which rotation is easily or not easily performed by force applied from the outside.

Figure 4A:
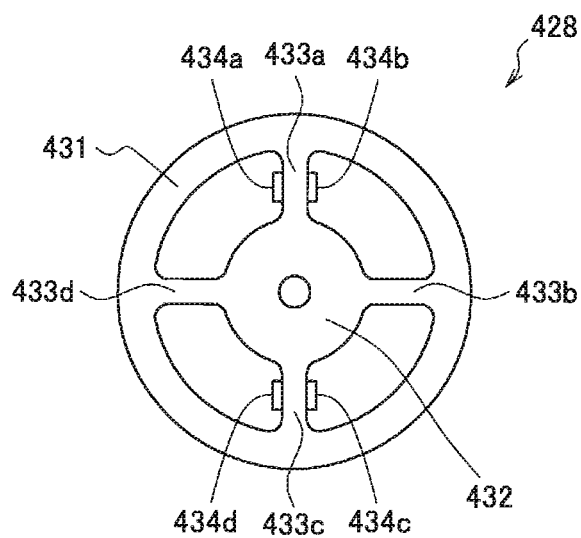
FIG. 4A is a schematic diagram schematically illustrating a state of a torque sensor illustrated in FIG. 3 viewed in an axis direction of a driving shaft.

Here, a configuration of the torque sensor 428 will be described in detail with reference to FIGS. 4A and 4B. FIG. 4A is a schematic diagram schematically illustrating a state of the torque sensor 428 illustrated in FIG. 3 viewed in the axis direction of the driving shaft 429.

Referring to FIG. 4A, the torque sensor 428 includes an outer ring section 431, an inner ring section 432, beam sections 433a to 433d, and distortion detecting elements 434a to 434d. As illustrated in FIG. 4A, the outer ring section 431 and the inner ring section 432 are concentrically arranged. In the present embodiment, the inner ring section 432 is connected to an input side, that is, the output shaft of the reduction gear 426, and the outer ring section 431 is connected to an output side, that is, an output member (not illustrated) at a subsequent stage.

The 4 beam sections 433a to 433d are arranged between the outer ring section 431 and the inner ring section 432 that are concentrically arranged, and connect the outer ring section 431 with the inner ring section 432. As illustrated in FIG. 4A, the beam sections 433a to 433d are interposed between the outer ring section 431 and the inner ring section 432 so that two neighboring sections of the beam sections 433a to 433d form an angle of 90°.

The distortion detecting elements 434a to 434d are installed at the two sections facing each other, that is, disposed at an angle of 180° among the beam sections 433a to 433d. It is possible to detect the generated torque and the external torque of the actuator 430 based on a deformation amount of the beam sections 433a to 433d detected by the distortion detecting elements 434a to 434d.

In the example illustrated in FIG. 4A, among the beam sections 433a to 433d, the distortion detecting elements 434a and 434b are installed at the beam section 433a, and the distortion detecting elements 434c and 434d are installed at the beam section 433c. Further, the distortion detecting elements 434a and 434b are installed with the beam section 433a interposed therebetween, and the distortion detecting elements 434c and 434d are installed with the beam section 433c interposed therebetween. For example, the distortion detecting elements 434a to 434d are distortion gauges attached to the surfaces of the beam sections 433a and 433c, and detect geometric deformation amounts of the beam sections 433a and 433c based on a change in electrical resistance. As illustrated in FIG. 4A, the distortion detecting elements 434a to 434d are installed at 4 positions, and the detecting elements 434a to 434d configure a so-called Wheatstone bridge. Thus, since it is possible to detect distortion using a so-called four-gauge technique, it is possible to reduce influence of interference of shafts other than a shaft in which distortion is detected, eccentricity of the driving shaft 429, a temperature drift, or the like.

As described above, the beam sections 433a to 433d serve as a distortion inducing body whose distortion is detected. The type of the distortion detecting elements 434a to 434d according to the present embodiment is not limited to a distortion gauge, and any other element may be used. For example, the distortion detecting elements 434a to 434d may be elements that detect the deformation amounts of the beam sections 433a to 433d based on a change in magnetic characteristics.

Although not illustrated in FIGS. 3 and 4A, the following configuration may be applied in order to improve the detection accuracy of the generated torque and the external torque by the torque sensor 428. For example, when portions of the beam sections 433a to 433d which are connected with the outer ring section 431 are formed at a thinner thickness than other portions, since a support moment is released, linearity of a deformation amount to be detected is improved, and influence by a radial load is reduced. Further, when both the outer ring section 431 and the inner ring section 432 are supported by a housing through a bearing, it is possible to exclude an action of other axial force and a moment from both the input shaft and the output shaft. Further, in order to reduce another axial moment acting on the outer ring section 431, a support bearing may be arranged at the other end of the actuator 430 illustrated in FIG. 3, that is, a portion at which the encoder 427 is arranged.

The configuration of the torque sensor 428 has been described above with reference to FIG. 4A. As described above, through the configuration of the torque sensor 428 illustrated in FIG. 4A, it is possible to detect the generated torque and the external torque of the actuator 430 with a high degree of accuracy.

Here, in the present embodiment, the configuration of the torque sensor 428 is not limited to the configuration illustrated in FIG. 4A and may be any other configuration. Another exemplary configuration of the torque sensor applied to the actuator 430 other than the torque sensor 428 will be described with reference to FIG. 4B.

Figure 4B:
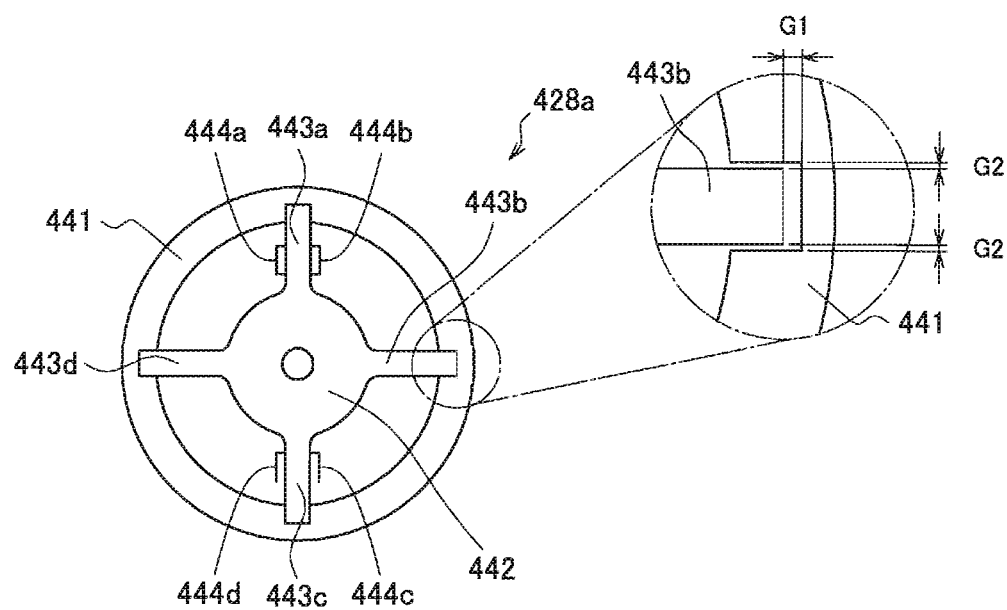
FIG. 4B is a schematic diagram illustrating another exemplary configuration of a torque sensor applied to the actuator illustrated in FIG. 3.

FIG. 4B is a schematic diagram illustrating another exemplary configuration of the torque sensor applied to the actuator 430 illustrated in FIG. 3. Referring to FIG. 4B, a torque sensor 428a according to the present modified example includes an outer ring section 441, an inner ring section 442, beam sections 443a to 443d, and distortion detecting elements 444a to 444d. FIG. 4B schematically illustrates a state of the torque sensor 428a viewed in the axis direction of the driving shaft 429, similarly to FIG. 4A.

In the torque sensor 428a, functions and configurations of the outer ring section 441, the inner ring section 442, the beam sections 443a to 443d, and the distortion detecting elements 444a to 444d are similar to the functions and the configurations of the outer ring section 431, the inner ring section 432, the beam sections 433a to 433d, and the distortion detecting elements 434a to 434d of the torque sensor 428 described above with reference to FIG. 4A. The torque sensor 428a according to the present modified example differs in a configuration of a connection portion of the beam sections 443a to 443d and the outer ring section 441. Thus, the torque sensor 428a illustrated in FIG. 4B will be described focusing on a configuration of the connection portion of the beam sections 443a to 443d and the outer ring section 441 that is the difference with the torque sensor 428 illustrated in FIG. 4A, and a description of a duplicated configuration will be omitted.

Referring to FIG. 4B, the connection portion of the beam section 443b and the outer ring section 441 is enlarged and illustrated together with a general view of the torque sensor 428a. In FIG. 4B, only the connection portion of the beam section 443b and the outer ring section 441 which is one of the four connection portions of the beam sections 443a to 443d and the outer ring section 441 is enlarged and illustrated, but the other 3 connection portions of the beam sections 443a, 443c, and 443d and the outer ring section 441 have the same configuration.

Referring to an enlarged view in FIG. 4B, in the connection portion of the beam section 443b and the outer ring section 441, an engagement concave portion is formed in the outer ring section 441, and the beam section 443b is connected with the outer ring section 441 such that the front edge of the beam section 443b is engaged with the engagement concave portion. Further, gaps G1 and G2 are formed between the beam section 443b and the outer ring section 441. The gap G1 indicates a gap between the beam section 443b and the outer ring section 441 in a direction in which the beam section 443b extends toward the outer ring section 441, and the gap G2 indicates a gap between the beam section 443b and the outer ring section 441 in a direction orthogonal to that direction.

As described above, in the torque sensor 428a, the beam sections 443a to 443d and the outer ring section 441 are arranged to be separated from each other with the certain gaps G1 and G2. In other words, in the torque sensor 428a, the outer ring section 441 is separated from the inner ring section 442. Thus, since the inner ring section 442 has a degree of freedom of a motion without being bound to the outer ring section 441, for example, even when vibration occurs at the time of driving of the actuator 430, a distortion by vibration can be absorbed by the air gaps G1 and G2 between the inner ring section 442 and the outer ring section 441. Thus, as the torque sensor 428a is applied as the torque sensor of the actuator 430, the generated torque and the external torque are detected with a high degree of accuracy.

For example, JP 2009-269102A and JP 2011-209099A which are patent applications previously filed by the present applicant can be referred to for the configuration of the actuator 430 corresponding to the ideal joint control illustrated in FIGS. 3, 4A, and 4B.

The schematic configuration of the robot arm apparatus 400 according to the present embodiment has been described above with reference to FIGS. 2, 3, 4A, and 4B. Next, the whole body cooperative control and the ideal joint control for controlling driving of the arm unit 420, that is, driving of the joint units 421a to 421f in the robot arm apparatus 400 according to the present embodiment, will be described.

[2-2. Generalized Inverse Dynamics]

Next, an overview of the generalized inverse dynamics used for the whole body cooperative control of the robot arm apparatus 400 according to the present embodiment will be described.

The generalized inverse dynamics are basic operations in whole body cooperative control of a multi-link structure of converting purposes of motion related to various dimensions in various kinds of operation spaces into torque to be generated by a plurality of joint units in view of various kinds of constraint conditions in a multi-link structure (for example, the arm unit 420 illustrated in FIG. 2 in the present embodiment) configured such that a plurality of links are connected by a plurality of joint units.

The operation space is an important concept in the force control of the robot apparatus. The operation space is a space for describing a relation between force acting on the multi-link structure and acceleration of the multi-link structure. When the driving control of the multi-link structure is performed by the force control rather than the position control, the concept of the operation space is necessary in the case in which a way of dealing with the multi-link structure and the environment is used as a constraint condition. The operation space is, for example, a space to which the multi-link structure belongs such as a joint space, a Cartesian space, or a momentum space.

The purpose of motion indicates a target value in the driving control of the multi-link structure, and, for example, a target value of a position, a speed, acceleration, force, or an impedance of the multi-link structure that is desired to be achieved through the driving control.

The constraint condition is a constraint condition related to, for example, a position, a speed, acceleration, or force of the multi-link structure that is decided by the shape or the structure of the multi-link structure, the environment around the multi-link structure, a setting performed by the user, or the like. For example, the constraint condition includes information about generated force, a priority, the presence or absence of a non-driven joint, vertical reactive force, a friction weight, a support polygon, and the like.

In the generalized inverse dynamics, in order to achieve both stability of numeric calculation and real-time processable operation efficiency, an operation algorithm is configured with a virtual force decision process (a virtual force calculating process) serving as a first stage and an actual force conversion process (an actual force calculating process) serving as a second stage. In the virtual force calculating process serving as the first stage, virtual force serving as virtual force that is necessary for achieving each purpose of motion and acts on the operation space is decided in view of a priority of a purpose of motion and a maximum value of the virtual force. In the actual force calculating process serving as the second stage, the calculated virtual force is converted into actual force that can be implemented by a configuration of an actual multi-link structure such as joint force or external force in view of a constraint related to a non-driven joint, vertical reactive force, a friction weight, a support polygon, or the like. The virtual force calculating process and the actual force calculating process will be described below. In the following description of the virtual force calculating process, the actual force calculating process, and the ideal joint control, for easier understanding, there are cases in which an exemplary configuration of the arm unit 420 of the robot arm apparatus 400 according to the present embodiment illustrated in FIGS. 2 and 3 is described as a specific example.

(2-2-1. Virtual Force Calculating Process)

A vector configured with certain physical quantities in the joint units of the multi-link structure is referred to as a "generalized variable q" (also referred to as a "joint value q" or a "joint space q"). An operation space x is defined by the following Equation (1) using a time differential value of the generalized variable q and a Jacobian J:

[Math 1]

$$\dot{x} = J\dot{q} \quad (1)$$

In the present embodiment, for example, q indicates a rotational angle in the joint units 421a to 421f of the arm unit 420. An equation of motion related to the operation space x is described by the following Equation (2):

[Math 2]

$$\ddot{x} = \Lambda^{-1} f + c \quad (2)$$

Here, f indicates force acting on the operation space x. Further, $\Lambda^{-1}$ indicates an operation space inertia inverse matrix, c indicates operation space bias acceleration, and $\Lambda^{-1}$ and c are expressed by the following Equations (3) and (4).

[Math 3]

$$\Lambda^{-1} = JH^{-1}J^T \quad (3)$$

$$c = JH^{-1}(\tau - b) + \dot{J}\dot{q} \quad (4)$$

H indicates a joint space inertia matrix, τ indicates joint force (for example, generated torque in the joint units 421a to 421f) corresponding to the joint value q, and b is a term indicating gravity, Coriolis force, or centrifugal force.

In the generalized inverse dynamics, the purpose of motion of the position and the speed related to the operation space x is known to be expressed as acceleration of the operation space x. At this time, in order to implement the operation space acceleration serving as the target value given as the purpose of motion from Equation (1), virtual force $f_v$ that has to act on the operation space x is obtained by solving a sort of linear complementary problem (LCP) expressed by the following Equation (5).

[Math 4]

$$w + \ddot{x} = \Lambda^{-1} f_v + c \quad (5)$$
s.t.
$$\begin{cases} ((w_i < 0) \cap (f_{v_i} = U_i)) \cup \\ ((w_i > 0) \cap (f_{v_i} = L_i)) \cup \\ ((w_i = 0) \cap (L_i < f_{v_i} < U_i)) \end{cases}$$

Here, $L_i$ and $U_i$ are set to a negative lower limit value (including $-\infty$) of an i-th component of $f_v$ and a positive upper limit value (including $+\infty$) of the i-th component of $f_v$. The LCP can be solved, for example, using an iterative technique, a pivot technique, a method using robust acceleration control, or the like.

Further, the operation space inertia inverse matrix $\Lambda^{-1}$ and the bias acceleration c are large in a calculation cost when they are calculated as in Equations (3) and (4) serving as definitional equations. Thus, a method of performing the calculation process of the operation space inertia inverse matrix $\Lambda^{-1}$ at a high speed by applying a quasidynamics calculation (FWD) of calculating generalized acceleration (joint acceleration) from generalized force (the joint force τ) of the multi-link structure has been proposed. Specifically, the operation space inertia inverse matrix $\Lambda^{-1}$ and the bias acceleration c can be obtained based on information related to force acting on the multi-link structure (for example, the arm unit 420 and the joint units 421a to 421f) such as the joint space q, the joint force τ, or the gravity g using the forward dynamics calculation FWD. As described above, the operation space inertia inverse matrix $\Lambda^{-1}$ can be calculated with a calculation amount of O(N) on the number N of joint units by applying the forward dynamics calculation FWD related to the operation space.

Here, as a setting example of the purpose of motion, a condition for achieving the target value (indicated by adding a bar above a second order differential of x) of the operation space acceleration by the virtual force $f_{vi}$ of an absolute value $F_i$ or less can be expressed by the following Equation (6):

[Math 5]

$$L_i = -F_i,\ U_i = F_i,\ \ddot{x}_i = \bar{\ddot{x}}_i \qquad (6)$$

As described above, the purpose of motion related to the position and the speed of the operation space x can be represented as the target value of the operation space acceleration and is specifically expressed by the following Equation (7) (the target value of the position and the speed of the operation space x are indicated by adding a bar above x and a first order differential of x).

[Math 6]

$$\bar{\ddot{x}}_i = K_p(\bar{x}_i - x_i) + K_v(\bar{\dot{x}}_i - \dot{x}_i) \qquad (7)$$

It is also possible to set the purpose of motion related to the operation space (momentum, Cartesian relative coordinates, an interlocked joint, and the like) represented by a linear sum of other operation spaces using an approach of a decomposition operation space. Further, it is necessary to give priorities to competing purposes of motion. The LCP is solved for each priority or in ascending order of priorities, and it is possible to cause virtual force obtained from a previous LCP to act as known external force of a subsequent LCP.

(2-2-2. Actual Force Calculating Process)

In the actual force calculating process serving as the second stage of the generalized inverse dynamics, a process of replacing the virtual force $f_v$ obtained in (2-2-1. Virtual force decision process) with actual joint force and external force is performed. A condition of implementing generalized force $\tau_v = J_v^T f_v$ based on virtual force through generated torque $\tau_a$ generated by the joint unit and external force $f_e$ is expressed by the following Equation (8).

[Math 7]

$$\begin{bmatrix} J_{vu}^T \\ J_{va}^T \end{bmatrix}(f_v - \Delta f_v) = \begin{bmatrix} J_{eu}^T \\ J_{ea}^T \end{bmatrix}f_e + \begin{bmatrix} 0 \\ \tau_a \end{bmatrix} \qquad (8)$$

Here, a subscript a indicates a set of driven joint units (a driven joint set), and a subscript u indicates a set of non-driven joint units (a non-driven joint set). In other words, the upper portions in Equation (8) represent balance of force of a space (a non-driven joint space) by the non-driven joint unit, and the lower portions represent balance of force of a space (a driven joint space) by the driven joint unit. $J_{vu}$ and $J_{va}$ indicate a non-driven joint component and a driven joint component of a Jacobian related to the operation space on which the virtual force $f_v$ acts, respectively. $J_{eu}$ and $J_{ea}$ indicate a non-driven joint component and a driven joint component of a Jacobian related to the operation space on which the external force $f_e$ acts. $\Delta f_v$ indicates a component of the virtual force $f_v$ that is hardly implemented by actual force.

The upper portions in Equation (8) are undefined, and, for example, $f_e$ and $\Delta f_v$ can be obtained by solving a quadratic programming problem (QP) expressed by the following Equation (9).

[Math 8]

$$\min \tfrac{1}{2}\varepsilon^T Q_1 \varepsilon + \tfrac{1}{2}\xi^T Q_2 \xi\ s.t.\ U\xi \geq v \qquad (9)$$

Here, $\varepsilon$ is a difference between sides of the upper portions in Equation (8), and indicates an equation error. $\xi$ is a connection vector of $f_e$ and $\Delta f_v$, and indicates a variable vector. $Q_1$ and $Q_2$ are positive definite symmetric matrices indicating weights at the time of minimization. Further, an inequality constraint of Equation (9) is used to express a constraint condition related to external force such as vertical reactive force, a friction cone, a maximum value of external force, and a support polygon. For example, an inequality constraint related to a rectangular support polygon is expressed by the following Equation (10).

[Math 9]

$$|F_x| \leq \mu_t F_z,\ |F_y| \leq \mu_t F_z,\ F_z \geq 0,\ |M_x| \leq d_y F_z,\ |M_y| \leq d_x F_z,$$
$$|M_z| \leq \mu_r F_z \qquad (10)$$

Here, z indicates a normal direction of a contact surface, and x and y indicate two orthogonal tangential directions that are vertical to z. $(F_x, F_y, F_z)$ and $(M_x, M_y, M_z)$ are external force and external force moment acting on a contact point. $\mu_t$ and $\mu_r$ indicate friction coefficients related to translation and rotation. $(d_x, d_y)$ indicates a size of a support polygon.

The solutions $f_e$ and $\Delta f_v$ of a minimum norm or a minimum error are obtained from Equations (9) and (10). It is possible to obtain the joint force $\tau_a$ necessary for implementing the purpose of motion by substituting $f_e$ and $\Delta f_v$ obtained from Equation (9) into the lower portion of Equation (8).

In the case of a system in which the basis is fixed, and there is no non-driven joint, all virtual force can be replaced only with joint force, and $f_e = 0$ and $\Delta f_v = 0$ can be set in Equation (8). In this case, the following Equation (11) can be obtained for the joint force $\tau_a$ from the lower portions in Equation (8).

[Math 10]

$$\tau_a = J_{va}^T f_v \qquad (11)$$

The whole body cooperative control using the generalized inverse dynamics according to the present embodiment has been described above. As described above, as the virtual force calculating process and the actual force calculating process are sequentially performed, it is possible to obtain the joint force $\tau_a$ for achieving a desired purpose of motion. In other words, conversely, as the calculated joint force $\tau_a$ is reflected in a theoretical model in motion of the joint units 421a to 421f, the joint units 421a to 421f are driven to achieve a desired purpose of motion.

Further, for example, JP 2009-95959A and JP 2010-188471A which are patent applications previously filed by the present applicant can be referred to for the whole body cooperative control using the generalized inverse dynamics described above, particularly, for the details of a process of deriving the virtual force $f_v$, a method of solving the LCP and obtaining the virtual force $f_v$, the resolution to the QP problem, and the like.

[2-3. Ideal Joint Control]

Next, the ideal joint control according to the present embodiment will be described. Motion of each of the joint units 421a to 421f is modelized by an equation of motion of a second order delay system of the following Equation (12):

[Math 11]

$$I_a \ddot{q} = \tau_a + \tau_e - \nu_a \dot{q} \qquad (12)$$

Here, $I_a$ indicates an inertia moment (inertia) in a joint unit, $\tau_a$ indicates generated torque of the joint units 421*a* to 421*f*, $\tau_e$ indicates external torque acting on each of the joint units 421*a* to 421*f*, and $v_e$ indicates a viscous drag coefficient in each of the joint units 421*a* to 421*f*. Equation (12) can also be regarded as a theoretical model representing motion of the actuator 430 in the joint units 421*a* to 421*f*.

As described above in [2-2. Generalized inverse dynamics], through the calculation using the generalized inverse dynamics, it is possible to calculate $\tau_a$ serving as actual force that each of the joint units 421*a* to 421*f* has to use to implement the purpose of motion using the purpose of motion and the constraint condition. Thus, ideally, a response according to the theoretical model expressed by Equation (12) is implemented, that is, a desired purpose of motion is achieved by applying each calculated $\tau_a$ to Equation (12).

However, practically, there are cases in which an error (a modelization error) between motion of the joint units 421*a* to 421*f* and the theoretical model expressed by Equation (12) occurs due to influence of various disturbances. The modelization error is classified into an error caused by a mass property such as a weight, a center of gravity, or a tensor of inertia of the multi-link structure and an error caused by friction, inertia, or the like in the joint units 421*a* to 421*f*. Of these, the modelization error of the former caused by the mass property can be relatively easily reduced at the time of construction of the theoretical model by applying high-accuracy computer aided design (CAD) data or an identification method.

Meanwhile, the modelization error of the latter caused by friction, inertia, or the like in the joint units 421*a* to 421*f* occurs due to a phenomenon that it is difficult to modelize, for example, friction or the like in the reduction gear 426 of the joint units 421*a* to 421*f*, and an unignorable modelization error may remain at the time of construction of the theoretical model. Further, there is likely to be an error between a value of an inertia $I_a$ or a viscous drag coefficient $v_e$ in Equation (12) and an actual value in the joint units 421*a* to 421*f*. The error that is hardly modeled may act as a disturbance in the driving control of the joint units 421*a* to 421*f*. Thus, due to influence of such a disturbance, practically, there are cases in which motion of the joint units 421*a* to 421*f* does not respond as in the theoretical model expressed by Equation (12). Thus, there are cases in which it is difficult to achieve the purpose of motion of the control target even when the actual force $\tau_a$ serving as the joint force calculated by the generalized inverse dynamics is applied. In the present embodiment, an active control system is added to each of the joint units 421*a* to 421*f*, and thus the response of the joint units 421*a* to 421*f* is considered to be corrected such that an ideal response according to the theoretical model expressed by Equation (12) is performed. Specifically, in the present embodiment, torque control of a friction compensation type using the torque sensors 428 and 428*a* of the joint units 421*a* to 421*f* is performed, and in addition, it is possible to perform an ideal response according to an ideal value even on the inertia $I_a$ and the viscous drag coefficient $v_a$ for the requested generated torque $\tau_a$ and the requested external torque $\tau_e$.

In the present embodiment, controlling driving of the joint unit such that the joint units 421*a* to 421*f* of the robot arm apparatus 400 perform the ideal response expressed by Equation (12) is referred to as the ideal joint control as described above. Here, in the following description, an actuator whose driving is controlled by the ideal joint control is also referred to as a "virtualized actuator (VA)" since the ideal response is performed. The ideal joint control according to the present embodiment will be described below with reference to FIG. 5.

Figure 5:
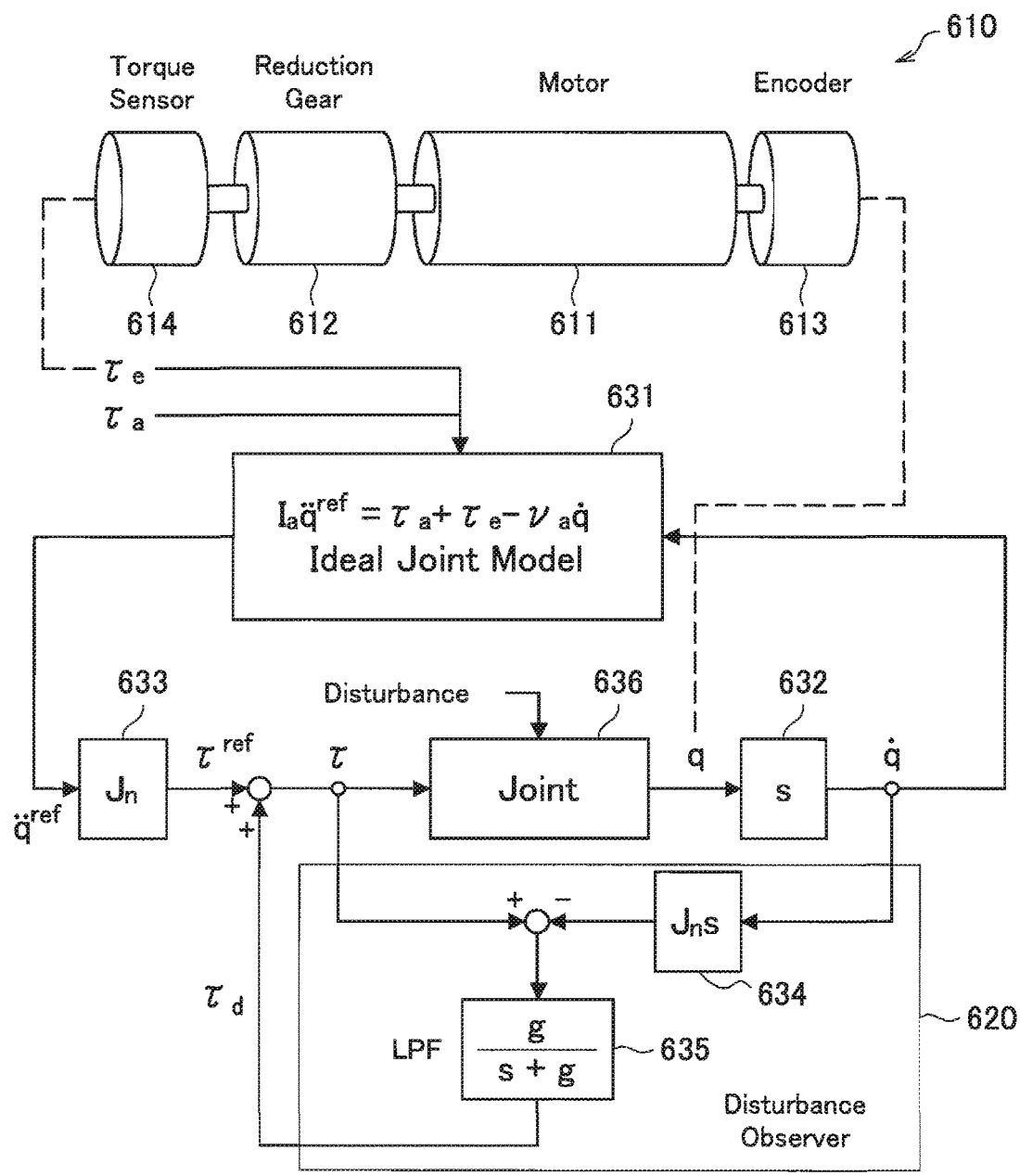
FIG. 5 is an explanatory diagram for describing ideal joint control according to an embodiment of the present disclosure.

FIG. 5 is an explanatory diagram for describing the ideal joint control according to an embodiment of the present disclosure. FIG. 5 schematically illustrates a conceptual computing unit that performs various kinds of operations according to the ideal joint control using blocks.

Referring to FIG. 5, an actuator 610 schematically illustrates a mechanism of the actuator 430 illustrated in FIG. 3, and a motor 611, a reduction gear 612, an encoder 613, and a torque sensor 614 correspond to the motor 424, the reduction gear 426, the encoder 427, and the torque sensor 428 (or the torque sensor 428*a* illustrated in FIG. 4B) which are illustrated in FIG. 3.

Here, when the actuator 610 performs the response according to the theoretical model expressed by Equation (12), it means that the rotational angular acceleration at the left side is achieved when the right side of Equation (12) is given. Further, as expressed in Equation (12), the theoretical model includes an external torque term $\tau_e$ acting on the actuator 610. In the present embodiment, in order to perform the ideal joint control, the external torque $\tau_e$ is measured by the torque sensor 614. Further, a disturbance observer 620 is applied to calculate a disturbance estimation value $\tau_d$ serving as an estimation value of torque caused by a disturbance based on a rotational angle q of the actuator 610 measured by the encoder 613.

A block 631 represents a computing unit that performs an operation according to the ideal joint model of the joint units 421*a* to 421*f* expressed by Equation (12). The block 631 can receive the generated torque $\tau_a$, the external torque $\tau_e$, and the rotational angular velocity (the first order differential of the rotational angle q) and output the rotational angular acceleration target value (a second order differential of a rotational angle target value $q^{ref}$) shown at the left side of Equation (12).

In the present embodiment, the generated torque $\tau_a$ calculated by the method described in [2-2. Generalized inverse dynamics] and the external torque $\tau_e$ measured by the torque sensor 614 are input to the block 631. Meanwhile, the rotational angle q measured by the encoder 613 is input to a block 632 indicating a computing unit that performs differential operation, and thus the rotational angular velocity (the first order differential of the rotational angle q) is calculated. In addition to the generated torque $\tau_a$ and the external torque $\tau_e$, the rotational angular velocity calculated by the block 632 is input to the block 631, and thus the rotational angular acceleration target value is calculated by the block 631. The calculated rotational angular acceleration target value is input to a block 633.

The block 633 indicates a computing unit that calculates torque to be generated in the actuator 610 based on the rotational angular acceleration of the actuator 610. In the present embodiment, specifically, the block 633 can obtain a torque target value $\tau^{ref}$ by multiplying a nominal inertia $J_n$ of the actuator 610 to the rotational angular acceleration target value. In the ideal response, a desired purpose of motion is achieved by causing the actuator 610 to generate the torque target value $\tau^{ref}$, but there are cases in which an actual response is influenced by a disturbance or the like as described above. Thus, in the present embodiment, the disturbance estimation value $\tau_d$ is calculated by the disturbance observer 620, and the torque target value $\tau^{ref}$ is corrected using the disturbance estimation value $\tau_d$.

A configuration of the disturbance observer 620 will be described. As illustrated in FIG. 5, the disturbance observer 620 calculates the disturbance estimation value $\tau_d$ based on a torque command value $\tau$ and the rotational angular velocity calculated from the rotational angle q measured by the encoder 613. Here, the torque command value $\tau$ is a torque value to be finally generated by the actuator 610 after influence of the disturbance is corrected. For example, when no disturbance estimation value $\tau_d$ is calculated, the torque command value $\tau$ is used as the torque target value $\tau^{ref}$.

The disturbance observer 620 is configured with a block 634 and a block 635. The block 634 is a computing unit that calculates torque to be generated by the actuator 610 based on the rotational angular velocity of the actuator 610. In the present embodiment, specifically, the rotational angular velocity calculated by the block 632 based on the rotational angle q measured by the encoder 613 is input to the block 634. The block 634 can obtain the rotational angular acceleration by performing an operation expressed by a transfer function $J_n s$, that is, by differentiating the rotational angular velocity, and calculate an estimation value (a torque estimation value) of torque actually acting on the actuator 610 by multiplying the calculated rotational angular acceleration by the nominal inertia $J_n$.

In the disturbance observer 620, a difference between the torque estimation value and the torque command value $\tau$ is obtained, and thus the disturbance estimation value $\tau_d$ serving as a value of torque by a disturbance is estimated. Specifically, the disturbance estimation value $\tau_d$ may be a difference between the torque command value $\tau$ in the previous control and the torque estimation value in the current control. Since the torque estimation value calculated by the block 634 is based on an actual measurement value, and the torque command value $\tau$ calculated by the block 633 is based on the ideal theoretical model of the joint units 421a to 421f indicated by the block 631, it is possible to estimate influence of a disturbance that is not considered in the theoretical model by obtaining the difference of the two values.

The disturbance observer 620 is further provided with a low pass filter (LPF) indicated by the block 635 in order to prevent a divergence of a system. The block 635 performs an operation represented by a transfer function g/(s+g), outputs only a low frequency component in response to an input value, and stabilizes a system. In the present embodiment, a difference value between the torque estimation value calculated by the block 634 and the torque command value $\tau^{ref}$ is input to the block 635, and the low frequency component is calculated as the disturbance estimation value $\tau_d$.

In the present embodiment, feedforward control of adding the disturbance estimation value $\tau_d$ calculated by the disturbance observer 620 to the torque target value $\tau^{ref}$ is performed, and thus the torque command value $\tau$ serving as a torque value to be finally generated by the actuator 610 is calculated. Then, the actuator 610 is driven based on the torque command value $\tau$. Specifically, the torque command value $\tau$ is converted into a corresponding electric current value (an electric current command value), the electric current command value is applied to the motor 611, so that the actuator 610 is driven.

By employing the configuration described above with reference to FIG. 5, in the driving control of the joint units 421a to 421f according to the present embodiment, even when there is a disturbance component such as friction, it is possible for the response of the actuator 610 to follow the target value. Further, it is possible to perform the ideal response according to the inertia $I_a$ and the viscous drag coefficient $v_a$ assumed by the theoretical model in the driving control of the joint units 421a to 421f.

For example, JP 2009-269102A that is a patent application previously filed by the present applicant can be referred to for the details of the above-described ideal joint control.

The ideal joint control according to the present embodiment has been described above with reference to FIG. 5 together with the generalized inverse dynamics used in the present embodiment. As described above, in the present embodiment, the whole body cooperative control of calculating driving parameters (for example, the generated torque values of the joint units 421a to 421f) of the joint units 421a to 421f for achieving the purpose of motion of the arm unit 420 is performed in view of the constraint condition using the generalized inverse dynamics. Further, as described above with reference to FIG. 5, in the present embodiment, as correction in which influence of a disturbance is considered is performed on the generated torque value calculated by the whole body cooperative control using the generalized inverse dynamics, the ideal joint control of implementing the ideal response based on the theoretical model in the driving control of the joint units 421a to 421f is performed. Thus, in the present embodiment, it is possible to perform high-accuracy driving control for achieving the purpose of motion for driving of the arm unit 420.

[2-4. Configuration of Robot Arm Control System]

Next, a configuration of the robot arm control system according to the present embodiment in which the whole body cooperative control and the ideal joint control described in [2-2. Generalized inverse dynamics] and [2-3. Ideal joint control] are applied to the driving control of the robot arm apparatus will be described.

Figure 6:
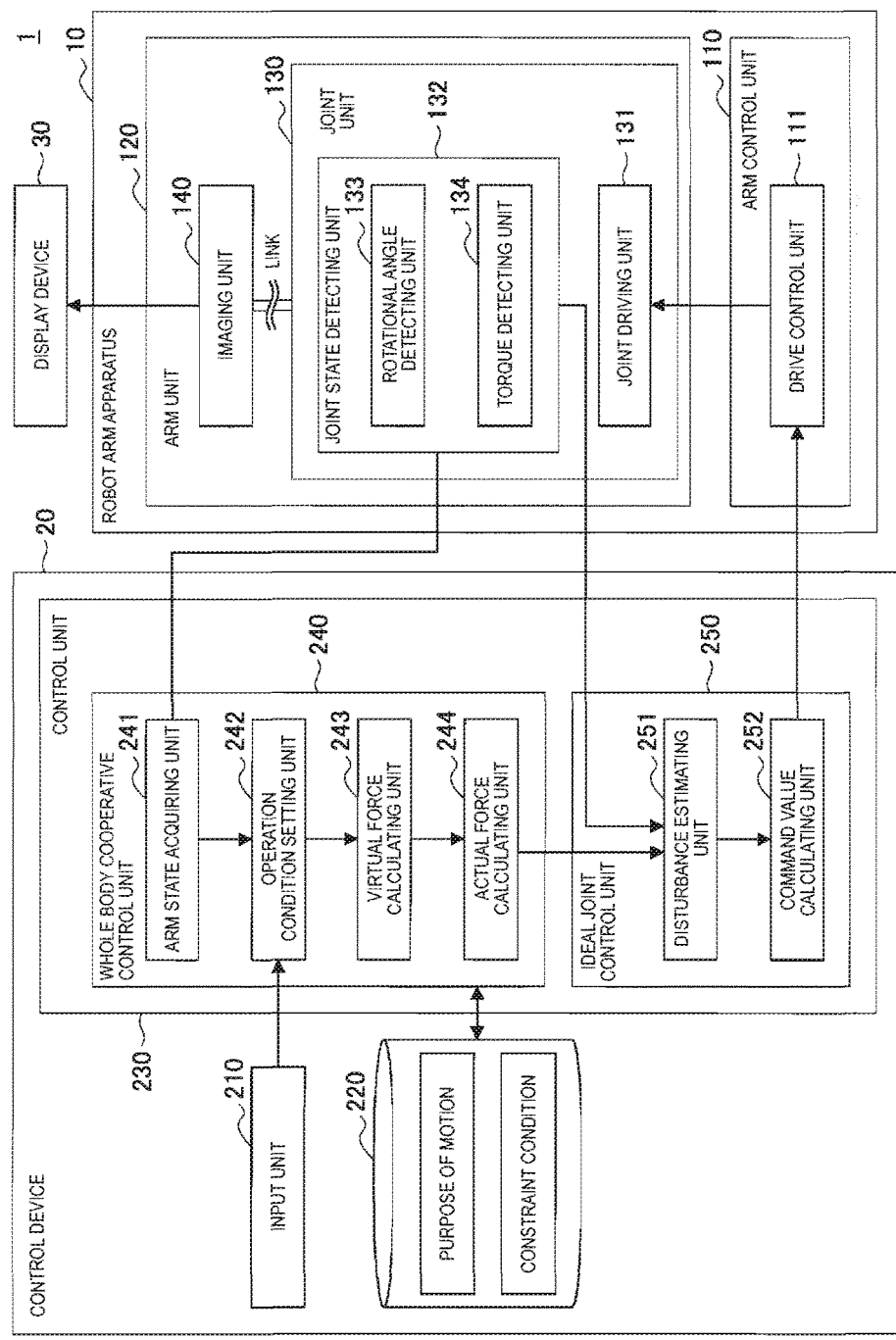
FIG. 6 is a functional block diagram illustrating an exemplary configuration of a robot arm control system according to an embodiment of the present disclosure.

An exemplary configuration of the robot arm control system according to an embodiment of the present disclosure will be described with reference to FIG. 6. FIG. 6 is a functional block diagram illustrating an exemplary configuration of the robot arm control system according to an embodiment of the present disclosure. In the robot arm control system illustrated in FIG. 6, components related to driving control of the arm unit of the robot arm apparatus are mainly illustrated.

Referring to FIG. 6, a robot arm control system 1 according to an embodiment of the present disclosure includes a robot arm apparatus 10, a control device 20, and a display device 30. In the present embodiment, various kinds of operations in the whole body cooperative control described in [2-2. Generalized inverse dynamics] and the ideal joint control described in [2-3. Ideal joint control] through the control device 20 are performed, and driving of the arm unit of the robot arm apparatus 10 is controlled based on the operation result. Further, the arm unit of the robot arm apparatus 10 is provided with an imaging unit 140 which will be described later, and an image captured by the imaging unit 140 is displayed on a display screen of the display device 30. Next, configurations of the robot arm apparatus 10, the control device 20, and the display device 30 will be described in detail. Note that in this specification, a system including a robot arm apparatus 10 and a control device 20 is designated simply a robot arm apparatus in some cases.

The robot arm apparatus 10 includes an arm unit having a multi-link structure configured with a plurality of joint units and a plurality of links, and drives the arm unit in the movable range to control the position and posture of the front edge unit installed at the front edge of the arm unit. The robot arm apparatus 10 corresponds to the robot arm apparatus 400 illustrated in FIG. 2.

Referring to FIG. 6, the robot arm apparatus 10 includes an arm control unit 110 and an arm unit 120. The arm unit 120 includes a joint unit 130 and the imaging unit 140.

The arm control unit 110 controls the robot arm apparatus 10 in an integrated manner, and controls driving of the arm unit 120. The arm control unit 110 corresponds to the control unit (not illustrated in FIG. 2) described above with reference to FIG. 2. Specifically, the arm control unit 110 includes a drive control unit 111, and controls driving of the arm unit 120, and driving of the arm unit 120 is controlled by controlling driving of the joint unit 130 according to control of the drive control unit 111. More specifically, the drive control unit 111 controls the number of revolutions of the motor in the actuator of the joint unit 130 and the rotational angle and the generated torque of the joint unit 130 by controlling an amount of electric current supplied to the motor. Here, as described above, driving control of the arm unit 120 by the drive control unit 111 is performed based on the operation result in the control device 20. Thus, an amount of electric current that is controlled by the drive control unit 111 and supplied to the motor in the actuator of the joint unit 130 is an amount of electric current decided based on the operation result in the control device 20.

The arm unit 120 has a multi-link structure configured with a plurality of joint units and a plurality of links, and driving of the arm unit 120 is controlled according to control of the arm control unit 110. The arm unit 120 corresponds to the arm unit 420 illustrated in FIG. 2. The arm unit 120 includes the joint unit 130 and the imaging unit 140. Further, since the plurality of joint units of the arm unit 120 have the same function and configuration, a configuration of one joint unit 130 representing the plurality of joint units is illustrated in FIG. 6.

The joint unit 130 connects links to be rotatable in the arm unit 120, and the rotary driving of the joint unit 130 is controlled according to control of the arm control unit 110 such that the arm unit 120 is driven. The joint unit 130 corresponds to the joint units 421a to 421f illustrated in FIG. 2. Further, the joint unit 130 includes an actuator, and the actuator has a configuration similar to, for example, the configuration illustrated in FIGS. 3, 4A, and 4B.

The joint unit 130 includes a joint driving unit 131 and a joint state detecting unit 132.

The joint driving unit 131 is a driving mechanism in the actuator of the joint unit 130, and as the joint driving unit 131 is driven, the joint unit 130 is rotationally driven. The drive control unit 111 controls driving of the joint driving unit 131. For example, the joint driving unit 131 is a component corresponding to the motor 424 and the motor driver 425 illustrated in FIG. 3, and driving the joint driving unit 131 corresponds to the motor driver 425 driving the motor 424 with an amount of electric current according to a command given from the drive control unit 111, The joint state detecting unit 132 detects the state of the joint unit 130. Here, the state of the joint unit 130 may mean a motion state of the joint unit 130. For example, the state of the joint unit 130 includes information such as the rotational angle, the rotational angular velocity, the rotational angular acceleration, and the generated torque of the joint unit 130. In the present embodiment, the joint state detecting unit 132 includes a rotational angle detecting unit 133 that detects the rotational angle of the joint unit 130 and a torque detecting unit 134 that detects the generated torque and the external torque of the joint unit 130. The rotational angle detecting unit 133 and the torque detecting unit 134 correspond to the encoder 427 of the actuator 430 illustrated in FIG. 3 and the torque sensors 428 and 428a illustrated in FIGS. 4A and 4B. The joint state detecting unit 132 transmits the detected state of the joint unit 130 to the control device 20.

The imaging unit 140 is an example of the front edge unit installed at the front edge of the arm unit 120, and acquires an image of a photographing target. The imaging unit 140 corresponds to the imaging unit 423 illustrated in FIG. 2. Specifically, the imaging unit 140 is, for example, a camera capable of photographing a photographing target in a moving image format or a still image format. More specifically, the imaging unit 140 includes a plurality of light receiving elements arranged two dimensionally, and can perform photoelectric conversion in the light receiving elements and acquire an image signal indicating an image of a photographing target. The imaging unit 140 transmits the acquired image signal to the display device 30.

Further, similarly to the robot arm apparatus 400 of FIG. 2 in which the imaging unit 423 is installed at the front edge of the arm unit 420, in the robot arm apparatus 10, the imaging unit 140 is actually installed at the front edge of the arm unit 120. In FIG. 6, the form in which the imaging unit 140 is installed at the front edge of the last link through the plurality of joint units 130 and a plurality of links is represented by schematically illustrating the link between the joint unit 130 and the imaging unit 140.

Further, in the present embodiment, various kinds of medical apparatuses may be connected to the front edge of the arm unit 120 as the front edge unit. As the medical apparatus, for example, there are various kinds of units used when the medical procedure is performed such as various kinds of medical procedure instruments including a scalpel or forceps or one unit of various kinds of examination apparatuses including a probe of an ultrasonic examination apparatus. Further, in the present embodiment, the imaging unit 140 illustrated in FIG. 6 or a unit having an imaging function such as an endoscope or a microscope may also be included as a medical apparatus. As described above, the robot arm apparatus 10 according to the present embodiment may be a medical robot arm apparatus including a medical apparatus. Similarly, the robot arm control system 1 according to the present embodiment may be a medical robot arm control system. Further, a stereo camera including two imaging units (camera units) may be installed at the front edge of the arm unit 120, and photography may be performed so that an imaging target is displayed as a 3D image.

The function and configuration of the robot arm apparatus 10 have been described above. Next, a function and configuration of the control device 20 will be described. Referring to FIG. 6, the control device 20 includes an input unit 210, a storage unit 220, and a control unit 230.

The control unit 230 controls the control device 20 in an integrated manner, and performs various kinds of operations for controlling driving of the arm unit 120 in the robot arm apparatus 10. Specifically, in order to control driving of the arm unit 120 of the robot arm apparatus 10, the control unit 230 performs various kinds of operations in the whole body cooperative control and the ideal joint control. The function and configuration of the control unit 230 will be described below in detail, but the whole body cooperative control and the ideal joint control have already been described in [2-2. Generalized inverse dynamics] and [2-3. Ideal joint control], and thus a description thereof will be omitted here.

The control unit 230 includes a whole body cooperative control unit 240, and an ideal joint control unit 250.

The whole body cooperative control unit 240 performs various kinds of operations related to the whole body cooperative control using the generalized inverse dynamics.

In the present embodiment, the whole body cooperative control unit 240 acquires a state (an arm state) of the arm unit 120 based on the state of the joint unit 130 detected by the joint state detecting unit 132. Further, the whole body cooperative control unit 240 calculates a control value for the whole body cooperative control of the arm unit 120 in the operation space based on the arm state and the purpose of motion and the constraint condition of the arm unit 120 using the generalized inverse dynamics. For example, the operation space refers to a space for describing a relation between force acting on the arm unit 120 and acceleration generated in the arm unit 120.

The whole body cooperative control unit 240 includes an arm state acquiring unit 241, an operation condition setting unit 242, a virtual force calculating unit 243, and an actual force calculating unit 244.

The arm state acquiring unit 241 acquires the state (the arm state) of the arm unit 120 based on the state of the joint unit 130 detected by the joint state detecting unit 132. Here, the arm state may mean the motion state of the arm unit 120. For example, the arm state includes information such as a position, a speed, acceleration, or force of the arm unit 120. As described above, the joint state detecting unit 132 acquires information such as the rotational angle, the rotational angular velocity, the rotational angular acceleration, or the generated torque of each of the joint units 130 as the state of the joint unit 130. Further, as will be described later, the storage unit 220 stores various kinds of information that is processed by the control device 20, and in the present embodiment, the storage unit 220 may store various kinds of information (arm information) related to the arm unit 120, for example, the number of joint units 130 and the number of links configuring the arm unit 120, a connection state of the link and the joint unit 130, and the length of the link. The arm state acquiring unit 241 can acquire the corresponding information from the storage unit 220. Thus, the arm state acquiring unit 241 can acquire information such as the positions (coordinates) of the plurality of joint units 130, a plurality of links, and the imaging unit 140 on the space (that is, the shape of the arm unit 120 or the position and posture of the imaging unit 140) or force acting on each of the joint units 130, the link, and the imaging unit 140 based on the state of the joint unit 130 and the arm information. The arm state acquiring unit 241 transmits the acquired arm information to the operation condition setting unit 242.

The operation condition setting unit 242 sets an operation condition in an operation related to the whole body cooperative control using the generalized inverse dynamics. Here, the operation condition may be the purpose of motion and the constraint condition. The purpose of motion may be various kinds of information related to a motion of the arm unit 120. Specifically, the purpose of motion may be a target value of the position and posture (coordinates), a speed, acceleration, and force of the imaging unit 140 or a target value of the position (coordinates), a speed, acceleration, and force of the plurality of joint units 130 and a plurality of links of the arm unit 120. The constraint condition may be various kinds of information for constricting the motion of the arm unit 120. Specifically, the constraint condition may be coordinates of a region into which none of the components of the arm unit should move, values of a speed and acceleration at which the arm unit should not move, a value of force that should not be generated, or the like. Further, a constraint range of various kinds of physical quantities in the constraint condition may be set from ones that are difficult for the arm unit 120 to implement structurally or may be appropriately set by the user. Further, the operation condition setting unit 242 includes a physical model (for example, one in which the number of links configuring the arm unit 120, the length of the link, the connection state of the link through the joint unit 130, the movable range of the joint unit 130, and the like are modelized) for the structure of the arm unit 120, and may set the motion condition and the constraint condition by generating a control model in which a desired motion condition and a desired constraint condition are reflected in the physical model.

In the present embodiment, it is possible to appropriately set the purpose of motion and the constraint condition and cause the arm unit 120 to perform a desired movement. For example, it is possible to set the target value of the position of the imaging unit 140 as the purpose of motion and move the imaging unit 140 to the target position, and it is also possible to set a movement constraint according to the constraint condition, for example, to prevent the arm unit 120 from invading a certain region in a space and then drive the arm unit 120.

As a specific example of the purpose of motion, for example, the purpose of motion may be a pivot movement serving as a turning movement in which the imaging unit 140 moves within a plane of a cone having a medical procedure part as an apex, and an axis of the cone is used as a pivot axis in a state in which the photographing direction of the imaging unit 140 is fixed to the medical procedure part. In the pivot movement, the turning movement may be performed in a state in which a distance between the imaging unit 140 and a point corresponding to the apex of the cone is maintained constant. As the pivot movement is performed, it is possible to observe an observation part at an equal distance and at different angles, and thus it is possible to improve a convenience of the user performing surgery.

Another specific example, the purpose of motion may be content controlling the generated torque in each of the joint units 130. Specifically, the purpose of motion may be a power assist movement of controlling the state of the joint unit 130 such that gravity acting on the arm unit 120 is negated and controlling the state of the joint unit 130 such that movement of the arm unit 120 is supported in a direction of force given from the outside. More specifically, in the power assist movement, driving of each of the joint units 130 is controlled such that each of the joint units 130 generates the generated torque for negating external torque by gravity in each of the joint units 130 of the arm unit 120, and thus the position and posture of the arm unit 120 are held in a certain state. When external torque is further applied from the outside (for example, from the user) in this state, driving of each of the joint units 130 is controlled such that each of the joint units 1 generates the generated torque in the same direction as the applied external torque. As the power assist movement is performed, when the user manually moves the arm unit 120, the user can move the arm unit 120 by small force, and thus a feeling of moving the arm unit 120 in a non-gravity state can be given to the user. Further, it is possible to combine the pivot movement with the power assist movement.

Here, in the present embodiment, the purpose of motion may mean a movement (motion) of the arm unit 120 implemented in the whole body cooperative control or may mean an instantaneous purpose of motion (that is, the target value in the purpose of motion) in the corresponding movement. For example, in the case of the pivot movement, performing the pivot movement by the imaging unit 140 is the purpose of motion, but, for example, a value of the position or the speed of the imaging unit 140 in the cone plane in the pivot movement is set as an instantaneous purpose of motion (the target value in the purpose of motion) while the pivot movement is being performed. Further, for example, in the case of the power assist movement, performing the power assist movement for supporting movement of the arm unit 120 in the direction of force applied from the outside is the purpose of motion, but a value of the generated torque in the same direction as the external torque applied to each of the joint units 130 is set as an instantaneous purpose of motion (the target value in the purpose of motion) while the power assist movement is being performed. In the present embodiment, the purpose of motion is a concept including both the instantaneous purpose of motion (for example, the target value of the position, the speed, or force of each component of the arm unit 120 during a certain period of time) and movement of each component of the arm unit 120 implemented over time as a result of continuously achieving the instantaneous purpose of motion. In each step in an operation for the whole body cooperative control in the whole body cooperative control unit 240, the instantaneous purpose of motion is set each time, and the operation is repeatedly performed, so that a desired purpose of motion is finally achieved.

Further, in the present embodiment, when the purpose of motion is set, the viscous drag coefficient in the rotary motion of each of the joint units 130 may be appropriately set as well. As described above, the joint unit 130 according to the present embodiment is configured to be able to appropriately adjust the viscous drag coefficient in the rotary motion of the actuator 430. Thus, as the viscous drag coefficient in the rotary motion of each of the joint units 130 is also set at the time of setting of the purpose of motion, for example, it is possible to implement the state in which rotation is easily or not easily performed by force applied from the outside. For example, in the case of the power assist movement, as the viscous drag coefficient in the joint unit 130 is set to be small, the user can move the arm unit 120 by small force, and the user can have a non-gravity feeling. As described above, the viscous drag coefficient in the rotary motion of each of the joint units 130 may be appropriately set according to content of the purpose of motion.

The specific examples of the purpose of motion will be described again in detail in [2-5. Specific example of purpose of motion].

Here, in the present embodiment, as will be described later, the storage unit 220 may store a parameter related to the operation condition such as the purpose of motion or the constraint condition used in an operation related to the whole body cooperative control. The operation condition setting unit 242 can set the constraint condition stored in the storage unit 220 as the constraint condition used in the operation of the whole body cooperative control.

Further, in the present embodiment, the operation condition setting unit 242 can set the purpose of motion by a plurality of methods. For example, the operation condition setting unit 242 may set the purpose of motion based on the arm state transmitted from the arm state acquiring unit 241. As described above, the arm state includes information of the position of the arm unit 120 and information of force acting on the arm unit 120. Thus, for example, when the user manually moves the arm unit 120, information related to how the user moves the arm unit 120 is also acquired as the arm state through the arm state acquiring unit 241. Thus, the operation condition setting unit 242 can set, for example, the position to which the user has moved the arm unit 120, a speed at which the user has moved the arm unit 120, or force by which the user has moved the arm unit 120 as the instantaneous purpose of motion based on the acquired arm state. As the purpose of motion is set as described above, control is performed such that driving of the arm unit 120 follows and supports movement of the arm unit 120 by the user.

Further, for example, the operation condition setting unit 242 may set the purpose of motion based on an instruction input from the input unit 210 by the user. As will be described later, the input unit 210 is an input interface through which the user inputs, for example, information or a command related to driving control of the robot arm apparatus 10 to the control device 20, and in the present embodiment, the purpose of motion may be set based on an operation input from the input unit 210 by the user. Specifically, the input unit 210 includes an operation unit operated by the user such as a lever or a pedal, and, for example, the operation condition setting unit 242 may set the position or the speed of each component of the arm unit 120 as the instantaneous purpose of motion according to an operation of the lever, the pedal, or the like.

Further, for example, the operation condition setting unit 242 may set the purpose of motion stored in the storage unit 220 as the purpose of motion used in the operation of the whole body cooperative control. For example, in the case of the purpose of motion for causing the imaging unit 140 to stop at a certain point in the space, coordinates of the certain point can be set as the purpose of motion in advance. Further, for example, in the case of the purpose of motion for causing the imaging unit 140 to move along a certain trajectory in the space, coordinates of points indicating the certain trajectory can be set as the purpose of motion in advance. As described above, when the purpose of motion can be set in advance, the purpose of motion may be stored in the storage unit 220 in advance. Further, for example, in the case of the pivot movement, the purpose of motion is limited to setting a position, a speed, or the like in the plane of the cone as the target value, and in the case of the power assist movement, the purpose of motion is limited to setting force as the target value. As described above, when the purpose of motion such as the pivot movement or the power assist movement is set in advance, for example, information related to a range or a type of the target value that can be set as the instantaneous purpose of motion in the purpose of motion may be stored in the storage unit 220. The operation condition setting unit 242 can include and set various kinds of information related to the purpose of motion as the purpose of motion.

Further, the user may appropriately set the method of setting the purpose of motion through the operation condition setting unit 242, for example, according to the purpose of the robot arm apparatus 10. Further, the operation condition setting unit 242 may set the purpose of motion and the constraint condition by appropriately combining the above methods. Furthermore, a priority of the purpose of motion may be set to the constraint condition stored in the storage unit 220, and when there are a plurality of different purposes of motion, the operation condition setting unit 242 may set the purpose of motion according to the priority of the constraint condition. The operation condition setting unit 242 transmits the arm state, the set purpose of motion and the constraint condition to the virtual force calculating unit 243.

The virtual force calculating unit 243 calculates virtual force in the operation related to the whole body cooperative control using the generalized inverse dynamics. For example, a virtual force calculation process performed by the virtual force calculating unit 243 may be a series of processes described above in (2-2-1. Virtual force calculating process). The virtual force calculating unit 243 transmits the calculated virtual force $f_v$ to the actual force calculating unit 244.

The actual force calculating unit 244 calculates actual force in the operation related to the whole body cooperative control using the generalized inverse dynamics. For example, an actual force calculation process performed by the actual force calculating unit 244 may be a series of processes described above in (2-2-2. Actual force calculating process). The actual force calculating unit 244 transmits the calculated actual force (the generated torque) $\tau_a$ to the ideal joint control unit 250. Further, in the present embodiment, the generated torque $\tau_a$ calculated by the actual force calculating unit 244 is also referred to as a "control value" or a "control torque value" to mean a control value of the joint unit 130 in the whole body cooperative control.

The ideal joint control unit 250 performs various kinds of operations related to the ideal joint control based on the generalized inverse dynamics. In the present embodiment, the ideal joint control unit 250 corrects influence of a disturbance on the generated torque $\tau_a$ calculated by the actual force calculating unit 244, and calculates the torque command value $\tau$ for implementing the ideal response of the arm unit 120. The operation process performed by the ideal joint control unit 250 corresponds to a series of processes described above in [2-3. Ideal joint control].

The ideal joint control unit 250 includes a disturbance estimating unit 251 and a command value calculating unit 252.

The disturbance estimating unit 251 calculates the disturbance estimation value $\tau_d$ based on the torque command value $\tau$ and the rotational angular velocity calculated from the rotational angle q detected by the rotational angle detecting unit 133. Here, the torque command value $\tau$ refers to the command value indicating the generated torque of the arm unit 120 that is finally transmitted to the robot arm apparatus 10. As described above, the disturbance estimating unit 251 has a function corresponding to the disturbance observer 620 illustrated in FIG. 5.

The command value calculating unit 252 calculates the torque command value $\tau$ serving as the command value indicating torque that is generated by the arm unit 120 and finally transmitted to the robot arm apparatus 10 using the disturbance estimation value $\tau_d$ calculated by the disturbance estimating unit 251. Specifically, the command value calculating unit 252 calculates the torque command value $\tau$ by adding the disturbance estimation value $\tau_d$ calculated by the disturbance estimating unit 251 to $\tau^{ref}$ calculated from the ideal model of the joint unit 130 expressed by Equation (12). For example, when the disturbance estimation value $\tau_d$ is not calculated, the torque command value $\tau$ is used as the torque target value $\tau^{ref}$. As described above, the function of the command value calculating unit 252 corresponds to a function other than that of the disturbance observer 620 illustrated in FIG. 5.

As described above, in the ideal joint control unit 250, a series of processes described above with reference to FIG. 5 is performed such that information is repeatedly exchanged between the disturbance estimating unit 251 and the command value calculating unit 252. The ideal joint control unit 250 transmits the calculated torque command value $\tau$ to the drive control unit 111 of the robot arm apparatus 10. The drive control unit 111 performs control of supplying an amount of electric current corresponding to the transmitted torque command value $\tau$ to the motor in the actuator of the joint unit 130, controls the number of revolutions of the motor, and controls the rotational angle and the generated torque of the joint unit 130.

In the robot arm control system 1 according to the present embodiment, since driving control of the arm unit 120 in the robot arm apparatus 10 is continuously performed while a task using the arm unit 120 is being performed, the above-described process is repeatedly performed in the robot arm apparatus 10 and the control device 20. In other words, the joint state detecting unit 132 of the robot arm apparatus 10 detects the state of the joint unit 130, and transmits the detected state of the joint unit 130 to the control device 20. In the control device 20, various kinds of operations related to the whole body cooperative control and the ideal joint control for controlling driving of the arm unit 120 are performed based on the state of the joint unit 130, the purpose of motion, and the constraint condition, and the torque command value $\tau$ serving as the operation result is transmitted to the robot arm apparatus 10. In the robot arm apparatus 10, driving of the arm unit 120 is controlled based on the torque command value $\tau$, and the state of the joint unit 130 during or after driving is detected by the joint state detecting unit 132 again.

The description of the other components of the control device 20 will now continue.

The input unit 210 is an input interface through which the user inputs, for example, information or a command related to driving control of the robot arm apparatus 10 to the control device 20. In the present embodiment, based on an operation input from the input unit 210 by the user, driving of the arm unit 120 of the robot arm apparatus 10 may be controlled, and the position and posture of the imaging unit 140 may be controlled. Specifically, as described above, as the user inputs instruction information related to an instruction of arm driving input from the input unit 210 to the operation condition setting unit 242, the operation condition setting unit 242 may set the purpose of motion in the whole body cooperative control based on the instruction information. As described above, the whole body cooperative control is performed using the purpose of motion based on the instruction information input by the user, and thus driving of the arm unit 120 according to the user's operation input is implemented.

Specifically, the input unit 210 includes an operation unit operated by the user such as a mouse, a keyboard, a touch panel, a button, a switch, a lever, and a pedal, for example. For example, when the input unit 210 includes a pedal, the user can control driving of the arm unit 120 by operating the pedal by foot. Thus, even when the user performs a treatment on the patient's medical procedure part using both hands, it is possible to adjust the position and posture of the imaging unit 140, that is, the photographing position or the photographing angle of the medical procedure part through an operation of the pedal by foot.

The storage unit 220 stores various kinds of pieces of information that are processed by the control device 20. In the present embodiment, the storage unit 220 can store various kinds of parameters used in the operation related to the whole body cooperative control and the ideal joint control performed by the control unit 230. For example, the storage unit 220 may store the purpose of motion and the constraint condition used in the operation related to the whole body cooperative control performed by the whole body cooperative control unit 240. The purpose of motion stored in the storage unit 220 may be a purpose of motion that can be set in advance so that the imaging unit 140 can stop at a certain point in the space as described above, for example. Further, the constraint condition may be set by the user in advance according to the geometric configuration of the arm unit 120, the purpose of the robot arm apparatus 10, or the like and then stored in the storage unit 220. Furthermore, the storage unit 220 may store various kinds of information related to the arm unit 120 used when the arm state acquiring unit 241 acquires the arm state. Moreover, the storage unit 220 may store, for example, the operation result in the operation related to the whole body cooperative control and the ideal joint control performed by the control unit 230 and numerical values calculated in the operation process. As described above, the storage unit 220 may store all parameters related to various kinds of processes performed by the control unit 230, and the control unit 230 can perform various kinds of processes while transmitting or receiving information to or from the storage unit 220.

The function and configuration of the control device 20 have been described above. The control device 20 according to the present embodiment may be configured, for example, with various kinds of information processing devices (arithmetic processing devices) such as a personal computer (PC) or a server. Next, a function and configuration of the display device 30 will be described.

The display device 30 displays various kinds of information on the display screen in various formats such as text or an image, and visually notifies the user of the information. In the present embodiment, the display device 30 displays an image captured by the imaging unit 140 of the robot arm apparatus 10 through the display screen. Specifically, the display device 30 includes a function or component such as an image signal processing unit (not illustrated) that performs various kinds of image processing on the image signal acquired by the imaging unit 140 or a display control unit (not illustrated) that performs control such that an image based on the processed image signal is displayed on the display screen. Further, the display device 30 may have various kinds of functions and components that are equipped in a general display device in addition to the above function or component. The display device 30 corresponds to the display device 550 illustrated in FIG. 1.

The functions and configurations of the robot arm apparatus 10, the control device 20, and the display device 30 according to the present embodiment have been described above with reference to FIG. 6. Each of the above components may be configured using a versatile member or circuit, and may be configured by hardware specialized for the function of each component. Further, all the functions of the components may be performed by a CPU or the like. Thus, a configuration to be used may be appropriately changed according to a technology level when the present embodiment is carried out.

As described above, according to the present embodiment, the arm unit 120 having the multi-link structure in the robot arm apparatus 10 has at least 6 or more degrees of freedom, and driving of each of the plurality of joint units 130 configuring the arm unit 120 is controlled by the drive control unit 111. Further, the medical apparatus is installed at the front edge of the arm unit 120. As driving of each joint unit 130 is controlled as described above, driving control of the arm unit 120 having a high degree of freedom is implemented, and the robot arm apparatus 10 for medical use having high operability for a user is implemented.

More specifically, according to the present embodiment, in the robot arm apparatus 10, the state of the joint unit 130 is detected by the joint state detecting unit 132. Further, in the control device 20, based on the state of the joint unit 130, the purpose of motion, and the constraint condition, various kinds of operations related to the whole body cooperative control using the generalized inverse dynamics for controlling driving of the arm unit 120 are performed, and torque command value τ serving as the operation result are calculated. Furthermore, in the robot arm apparatus 10, driving of the arm unit 120 is controlled based on the torque command value τ. As described above, in the present embodiment, driving of the arm unit 120 is controlled by the whole body cooperative control using the generalized inverse dynamics. Thus, driving control of the arm unit 120 according to the force control is implemented, and the robot arm apparatus having the high operability for the user is implemented. Further, in the present embodiment, in the whole body cooperative control, for example, control for implementing various kinds of purposes of motion for improving user convenience such as the pivot movement and the power assist movement can be performed. Furthermore, in the present embodiment, for example, various driving units for moving the arm unit 120 manually or through an operation input from a pedal are implemented, and thus user convenience is further improved.

Further, in the present embodiment, the whole body cooperative control and the ideal joint control are applied to driving control of the arm unit 120. In the ideal joint control, a disturbance component such as friction or inertia in the joint unit 130 is estimated, and feedforward control is performed using the estimated disturbance component. Thus, even when there is a disturbance component such as friction, the ideal response can be implemented on driving of the joint unit 130. Thus, small influence of vibration or the like, high-accuracy responsiveness, and high positioning accuracy or stability are implemented in driving control of the arm unit 120.

Further, in the present embodiment, each of the plurality of joint units 130 configuring the arm unit 120 has a configuration suitable for the ideal joint control illustrated in FIG. 3, for example, and the rotational angle, the generated torque and the viscous drag coefficient of each of the joint units 130 can be controlled according to an electric current value. As described above, driving of each of the joint units 130 is controlled according to an electric current value, and driving of each of the joint units 130 is controlled according to the whole body cooperative control while detecting the entire state of the arm unit 120, and thus the counter balance is unnecessary, and the small robot arm apparatus 10 is implemented.

[2-5. Specific Example of Purpose of Motion]

Next, a specific example of the purpose of motion according to the present embodiment will be described. As described above in [2-4. Configuration of the robot arm control system], in the present embodiment, various kinds of purposes of motion are implemented by the whole body cooperative control. Here, as a specific example of the purpose of motion according to the present embodiment, the power assist movement and the pivot movement will be described. In the following description of the specific example of the purpose of motion, components of the robot arm control system according to the present embodiment are indicated using reference numerals in the functional block diagram illustrated in FIG. 6.

The power assist movement is a movement of controlling the state of the joint unit 130 such that gravity acting on the arm unit 120 is negated and controlling the state of the joint unit 130 such that movement of the arm unit 120 in a direction of force applied from the outside is supported. Specifically, when the user manually moves the arm unit 120, the power assist movement is a movement of controlling driving of the arm unit 120 such that force applied by the user is supported. More specifically, in order to implement the power assist movement, first, external torque is detected by the torque detecting unit 134 in a state in which no force other than gravity acts on the arm unit 120, and the instantaneous purpose of motion is set so that the generated torque for negating the detected external torque is generated by each of the joint units 130. At this stage, the position and posture of the arm unit 120 are held in a certain state. When external torque is further applied from the outside (for example, from the user) in this state, additionally applied external torque is detected by the torque detecting unit 134, and the instantaneous purpose of motion is further set such that each of the joint units 130 generates generated torque in the same direction as the detected additional external torque. As driving of each of the joint units 130 is controlled according to the instantaneous purpose of motion, the power assist movement is implemented. Through the power assist movement, the user can move the arm unit by small force, and thus the user can have a feeling of moving the arm unit 120 in a non-gravity state, and the operability of the arm unit 120 by the user is improved.

The pivot movement is a turning movement in which the front edge unit installed at the front edge of the arm unit 120 moves on a plane of a cone having a certain point in the space as an apex in a state in which a direction of the front edge unit is fixed on the certain point, and an axis of the cone is used as a pivot axis. Specifically, when the front edge unit is the imaging unit 140, the pivot movement is a turning movement in which the imaging unit 140 installed at the front edge of the arm unit 120 moves on a plane of a cone having a certain point in a space as an apex in a state in which the photographing direction of the imaging unit 140 is fixed on the certain point, and an axis of the cone is used as a pivot axis. As a point corresponding to the apex of the cone in the pivot movement, for example, the medical procedure part is selected. Further, in the pivot movement, the turning movement may be performed in a state in which a distance between the front edge unit or the imaging unit 140 and the point corresponding to the apex of the cone is maintained constant. Further, since the direction of the front edge unit or the photographing direction of the imaging unit 140 is fixed on a certain point (for example, the medical procedure part) in the space, the pivot movement is also referred to as a "point lock movement."

<3. Control According to Visual Field Enlargement Factor>

Figure 7:
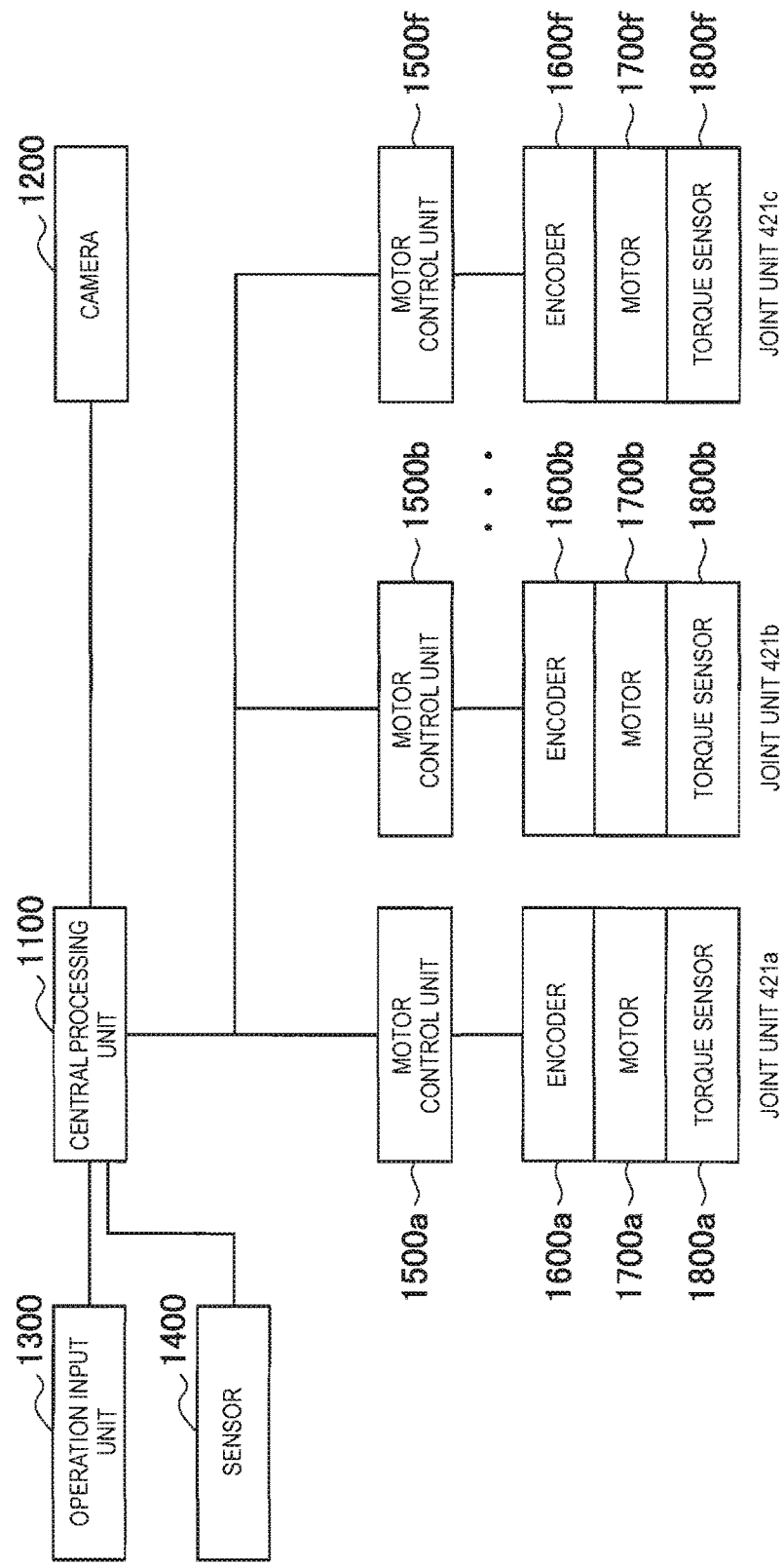
FIG. 7 is a schematic diagram illustrating a configuration of a specific system that adjusts a usability of a robot arm according to a zoom factor.

Next, control according to a visual field enlargement factor will be described. In the present embodiment, the usability of the robot arm by the user is adjusted according to the on-screen enlargement factor of a subject imaged by the imaging unit 140 (hereinafter, the visual field enlargement factor may be designated simply the enlargement factor in some cases). FIG. 7 is a schematic diagram illustrating a configuration of a specific system 1000 that adjusts a usability of a robot arm according to a visual field enlargement factor. The system 1000 illustrated in FIG. 7 includes a central processing unit (CPU) 1100, a camera 1200, an operation input unit 1300, a sensor 1400, motor control units 1500a, 1500b, . . . , 1500f, encoders 1600a, 1600b, . . . , 1600f, motors 1700a, 1700b, . . . , 1700f, and torque sensors 1800a, 1800b, . . . , 1800f.

The camera 1400 illustrated in FIG. 7 corresponds to the imaging unit 140 in FIG. 6. In addition, the encoder 1600a, the motor 1700a, and the torque sensor 1800a constitute the joint unit 421a. Similarly, the encoder 1600b, the motor 1700b, and the torque sensor 1800b constitute the joint unit 421b, while the encoder 1600f, the motor 1700f, and the torque sensor 1800f constitute the joint unit 421f.

The operation input unit 1300 corresponds to the input unit 210 in FIG. 6. The operation input unit 1300 is a switch, such as a remote control switch or a foot switch, for example. The sensor 1400 is mounted to the front edge of the arm unit 120 of the robot arm apparatus 10, for example, and is a sensor such as six-axis sensor that detects user operations.

Additionally, the central processing unit 1100 illustrated in FIG. 7 corresponds to the control unit 230 in FIG. 6. Also, each of the motor control units 1500a, 1500b, . . . , 1500f correspond to the arm control unit 110 in FIG. 6.

Additionally, the encoders 1600a, 1600b, . . . , 1600f included respectively in the joint units 421a, 421b, . . . , 421c correspond to the rotational angle detecting unit 133 in FIG. 6, while the motors 1800a, 1800b, . . . , 1800f included respectively in the joint units 421a, 421b, . . . , 421f correspond to the joint driving unit 131 in FIG. 6, and the torque sensors 1800a, 1800b, . . . , 1800f included respectively in the joint units 421a, 421b, . . . , 421f correspond to the torque detecting unit 134 in FIG. 6.

In the robot arm apparatus 10, the case of a high enlargement factor of an image captured by the camera 1200 is a state in which the subject is greatly enlarged. In such a state, since the operator is observing the enlarged subject more carefully, it is not preferable for the arm unit 120 of the robot arm apparatus 10 to move unexpectedly.

For this reason, in the present embodiment, the motion of each of the joint units 421a, 421b, . . . , 421f is controlled according to the enlargement factor. Specifically, the viscosity of the motion of each of the joint units 421a, 421b, . . . , 421f is controlled according to the enlargement factor. Additionally, the velocity of the motion and the amount of movement with respect to an operation of each of the joint units 421a, 421b, . . . , 421f are controlled according to the enlargement factor. The visual field enlargement factor may be calculated from distance information about the distance from the camera 1200 to the imaging target (subject) and the zoom factor (imaging magnification) of the camera 1200. Also, for the distance information to the subject, distance information according to autofocus obtained from the camera 1200, distance information according to stereo vision, distance information estimated from the arm orientation, distance information measured by some other sensor, such as a rangefinder sensor, or the like may be used. For example, if the zoom factor is at maximum and the camera 1200 is maximally close to the object, control that moves the slowest may be performed (that is, the lowest drive velocity or the highest viscosity is set), whereas if the distance between the camera 1200 and the subject is large, even under zoomed imaging, and a wide range is visible, operability is not reduced even with a high drive velocity or a low viscosity. When driving the joints, it is preferable to adjust the drive velocity and viscosity so that the rate of movement of the object always stays within a certain range, regardless of the apparent size of the object on-screen.

With viscosity control, control is performed to raise the viscosity of the motion of each of the joint units 421a, 421b, . . . , 421f to the extent that the enlargement factor by the camera 1200 is high. As the viscosity of the motion of each of the joint units 421a, 421b, . . . , 421f rises, an opposing force corresponding to the movement of the arm unit 120 is imparted to the operator, and the motion of the arm becomes sluggish. Thus, fine adjustment of the front edge of the arm unit 120 becomes easier to perform.

Consequently, the operator is able to make fine adjustments to the position of the camera 1200 with respect to the subject while checking an enlarged picture of the subject on the display device 30.

To control motion as above, information related to the enlargement factor is sent from the camera 1200 to the central processing unit 1100. In the central processing unit 1100, the operation condition setting unit 242 computes a value of viscosity according to the enlargement factor as the purpose of motion discussed earlier, Additionally, the processes discussed earlier are performed by the virtual force calculating unit 243 and the actual force calculating unit 244, a process is performed by the ideal joint control unit 250, and in addition, a torque command value t is computed based on the computed value of viscosity, and sent to each of the motor control units 1500a, 1500b, . . . , 1500c. The motor control units 1500a, 1500b, . . . , 1500f respectively control the motors 1700a, 1700b, . . . , 1700f based on the torque command value τ. As discussed earlier, the motor driver 425 of the robot arm apparatus 10 is able to adjust a viscous drag coefficient on rotary motion of the actuator 430 by adjusting the amount of current supplied to the motor 424.

Figure 8:
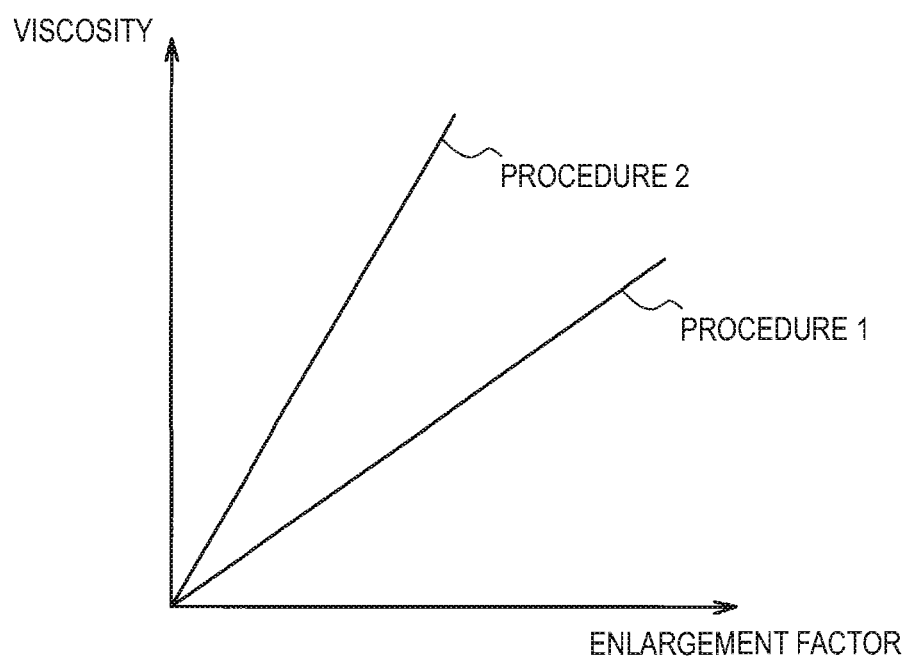
FIG. 8 is a schematic diagram illustrating an example of a map to use when a central processing unit computes a viscosity according to a zoom factor.

FIG. 8 is a schematic diagram illustrating an example of a map to use when the central processing unit 1100 computes a viscosity according to an enlargement factor. As illustrated in FIG. 8, a map is prescribed so that as the enlargement factor increases, the value of viscosity also increases. Also, as illustrated in FIG. 8, in cases such as when the robot arm apparatus 10 is used for medical surgery, different map characteristics may be prescribed depending on the surgical procedure. Consequently, in Procedure 1, which demands more high-precision operation of the robot arm apparatus 10, the ratio of the increase in viscosity with respect to the increase in enlargement factor is raised, thereby making it possible to make the motion of the arm unit 120 of the robot arm apparatus 10 more sluggish to make more high-precision fine adjustments. Note that the map illustrated in FIG. 8 may be stored in memory provided in the control device 20, Also, in FIG. 8, an example of switching the map depending on the surgical procedure is illustrated, but the map may also be switched in response to a user operation performed on the operation input unit 1300. Consequently, the user is able to set the motion (viscosity) of the arm unit 120 to the user's preferred state.

Additionally, when controlling velocity according to the enlargement factor, control is performed to lower the velocity of the motion of each of the joint units 421a, 421b, . . . , 421f to the extent that the enlargement factor by the camera 1200 is high. Consequently, since the velocity of the motion of each of the joint units 421a, 421b, . . . , 421f lowers as the enlargement factor rises, more high-precision fine adjustment of the arm unit 120 of the robot arm apparatus 10 becomes possible.

Similarly, when controlling the amount of movement with respect to an operation according to the enlargement factor, control is performed to decrease the amount of movement of the front edge of the arm unit 120 of the robot arm apparatus 10 to the extent that the enlargement factor by the camera 1200 is high. Consequently, since the amount of movement in the motion of each of the joint units 421a, 421b, . . . , 421f lowers as the enlargement factor rises, more high-precision fine adjustment of the robot arm apparatus 10 becomes possible.

Figure 14:
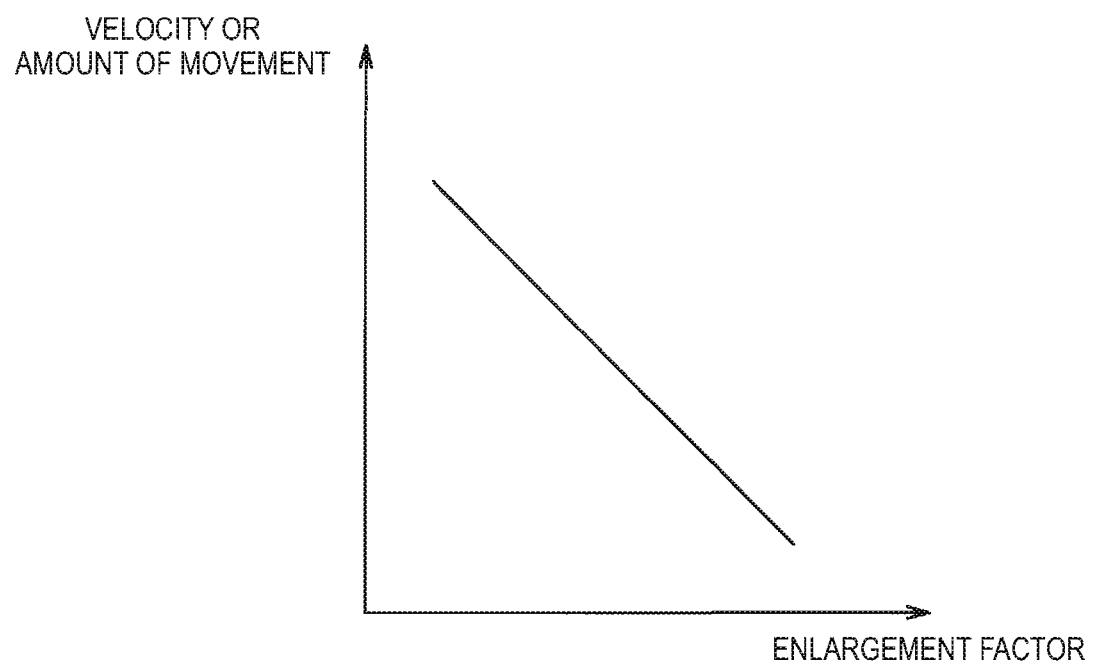
FIG. 14 is a schematic diagram illustrating an example of a map to use when a central processing unit computes a velocity and an amount of movement according to a zoom factor.

When controlling the velocity and the amount of movement according to the enlargement factor, the operation condition setting unit 242 computes the velocity and the amount of movement according to the enlargement factor as the purpose of motion discussed earlier. The velocity and the amount of movement according to the enlargement factor may be computed from the map illustrated in FIG. 14, for example. As illustrated in FIG. 14, the velocity and the amount of movement lower according to the enlargement factor. Additionally, the processes discussed earlier are performed by the virtual force calculating unit 243 and the actual force calculating unit 244, a process is performed by the ideal joint control unit 250, and a torque command value τ is output from the command value calculating unit 252 to the robot arm apparatus 10. The torque command value τ is sent to each of the motor control units 1500a, 1500b, . . . , 1500f The motor control units 1500a, 1500b, . . . , 1500f respectively control the motors 1700a, 1700b, . . . , 1700f based on the torque command value τ. Note that the amount of movement may refer to the amount of movement of the arm unit 120 corresponding to a single operation in the case in which the user performs remote control operations on the arm unit 120 using the operation input unit 1300, for example.

As above, in the present embodiment, by switching the viscosity, the movement velocity, the amount of movement (amount of movement of the arm unit 120 with respect to a single operation by the user), the acceleration, or other parameters according to the enlargement factor of the camera 1400, an opposing force according to the amount of movement of the arm unit 120 by a user operation may be returned to the operator, and operability may be improved. Consequently, when the enlargement factor is high, more fine-grained adjustments become possible. Also, when the enlargement factor is low, the arm unit 120 becomes easier to move, thereby making it possible to move the arm unit 120 rapidly so that a desired part of the subject is displayed on the display device 30.

In addition, control is also possible in which orientation information about the arm unit 120 is utilized and the viscosity is increased according to a magnitude shifted from a fixed distance, for example, in order to keep the distance between the subject and the front edge of the arm unit 120 a fixed distance.

Control according to the enlargement factor basically is performed when operating input from the user is detected. The detection of operating input may be conducted by detecting user operations performed on the operation input unit 1300 (primarily remote control operations). Also, the detection of operating input may be detected by the torque sensors 1800a, 1800b, . . . , 1800f when the user operates the arm unit 120. In addition, by sensing external force, it is also possible to switch from a state in which the arm unit 120 is locked to a mode in which the arm unit 120 moves with light operating force. If an electromagnetic brake function is included, the disengagement (or engagement) of the electromagnetic brake may also be conducted in conjunction with the state switch. Additionally, it is also possible to sense not only operations in the XY directions of the screen of the display device 30, but also force in the Z direction (the depth direction of the screen), and control the viscosity, velocity, acceleration, or amount of movement, or detect an operation in any of the XYZ directions with respect to the screen and change the focus position, the enlargement factor, or the camera position.

Detection of external force may include not only detection using the torque sensors 1800a, 1800b, . . . , 1800f respectively built into each of the joint units 421a, 421b, . . . , 421f, but may also be detected using a sensor such as a touch sensor installed on the arm unit 120, or a six-axis force sensor or a proximity sensor installed at the base or one the front edge of the arm unit 120. These sensors are included in the sensor 1400 illustrated in FIG. 7.

Additionally, the respective encoders 1600a, 1600b, . . . , 1600f of the joint units 421a, 421b, . . . , 421f may be utilized to pseudo-detect that the arm has been operated, based on position information and angular velocity detected from the encoders 1600a, 1600b, . . . , 1600f.

In addition, an operation by the operator may be not only an operation of moving the arm unit 120 directly, but also be detected by a sensor such as an infrared proximity sensor. Also, contactless operations using voice input, gestures, or hand movements are also possible. In this way, the operation input unit 1300 may also be a sensor that detects speech, or a sensor (six-axis force sensor) that detects contactless operations such as gestures or hand movements.

In the case of inputting operation information from the operation input unit 1300 with a remote control, components such as mechanical switches, jog dials, and analog sticks may be used as the operation input unit 1300. Furthermore, in the case of a configuration that works in conjunction with medical navigation, in which a target position of the arm unit 120 is input separately, for example, it is also possible to raise the viscosity when the front edge of the arm unit 120 comes close to the target position, and thereby notify the operator that the front edge has come near the target position.

In addition, various sensors that detect properties such as gaze, speech, brain wave, and facial expressions may be used as the sensor 1400. The arm unit 120 may be controlled based on detections by these sensors.

If there is interference, such as interference with an organ in the case in which the front edge of the robot arm apparatus 10 is used inside the body, or interference between the robot arm apparatus 10 and a tool or the like outside the body, it is also possible to suspend or make less responsive the movement of the arm unit 120, and by raising the opposing force and viscosity of the arm unit 120, notify the operator of the interference, and potentially improve safety.

<4. Processing Procedure of Robot Arm Control Method>

Figure 9:
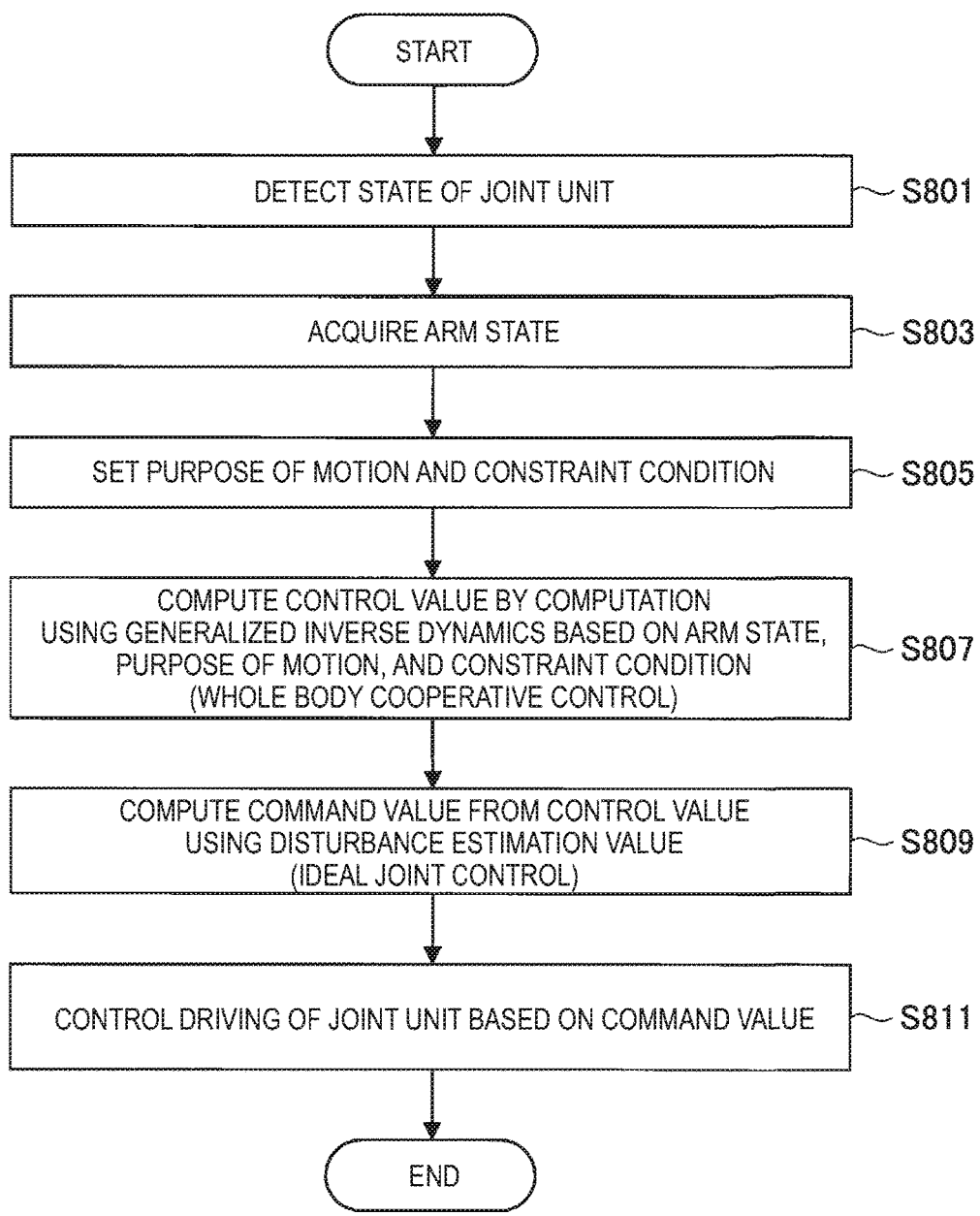
FIG. 9 is a flowchart illustrating a processing procedure of a robot arm control method.

Next, a processing procedure of a robot arm control method according to an embodiment of the present disclosure will be described with reference to FIG. 9. FIG. 9 is a flowchart illustrating a processing procedure of a robot arm control method according to an embodiment of the present disclosure. The following description will proceed with an example in which the robot arm control method according to the present embodiment is implemented through the configuration of the robot arm control system 1 illustrated in FIG. 6. Thus, the robot arm control method according to the present embodiment may be a medical robot arm control method. Further, in the following description of the processing procedure of the robot arm control method according to the present embodiment, the functions of the respective components of the robot arm control system 1 illustrated in FIG. 6 have already been described above in [2-4. Configuration of the robot arm control system], and thus a detailed description thereof is omitted.

Referring to FIG. 9, in the robot arm control method according to the present embodiment, first, in step S801, the joint state detecting unit 132 detects the state of the joint unit 130. Here, the state of the joint unit 130 refers to, for example, the rotational angle, the generated torque and/or the external torque in the joint unit 130.

Then, in step S803, the arm state acquiring unit 241 acquires the arm state based on the state of the joint unit 130 detected in step S801. The arm state refers to a motion state of the arm unit 120, and may be, for example, a position, a speed, or acceleration of each component of the arm unit 120, or force acting on each component of the arm unit 120.

Then, in step S805, the operation condition setting unit 242 sets the purpose of motion and the constraint condition used for the operation in the whole body cooperative control based on the arm state acquired in step S803. Further, the operation condition setting unit 242 may not set the purpose of motion based on the arm state, may set the purpose of motion based on the instruction information on driving of the arm unit 120 which is input, for example, from the input unit 210 by the user, and may use the purpose of motion previously stored in the storage unit 220. Furthermore, the purpose of motion may be set by appropriately combining the above methods. Moreover, the operation condition setting unit 242 may use the constraint condition previously stored in the storage unit 220.

Then, in step S807, the operation for the whole body cooperative control using the generalized inverse dynamics is performed based on the arm state, the purpose of motion, and the constraint condition, and a control value $\tau_a$ is calculated. The process performed in step S807 may be a series of processes in the virtual force calculating unit 243 and the actual force calculating unit 244 illustrated in FIG. 6, that is, a series of processes described above in [2-2. Generalized inverse dynamics].

Then, in step S809, the disturbance estimation value $\tau_d$ is calculated, the operation for the ideal joint control is performed using the disturbance estimation value $\tau_d$, and the command value $\tau$ is calculated based on the control value $\tau_a$. The process performed in step S809 may be a series of processes in the ideal joint control unit 250 illustrated in FIG. 6, that is, a series of processes described above in [2-3. Ideal joint control].

Lastly, in step S811, the drive control unit 111 controls driving of the joint unit 130 based on the command value $\tau$.

The processing procedure of the robot arm control method according to the present embodiment has been described above with reference to FIG. 9. In the present embodiment, the process of step S801 to step S811 illustrated in FIG. 9 is repeatedly performed while the task using the arm unit 120 is being performed. Thus, in the present embodiment, driving control of the arm unit 120 is continuously performed while the task using the arm unit 120 is being performed.

Next, a process of control according to the enlargement factor will be described based on FIG. 10. First, in step S10, it is determined whether or not operating input of at least a fixed value is detected. The detection of operating input is conducted by the respective torque sensors 1800a, 1800b, . . . , 1800f of the joint units 421a, 421b, . . . , 421f. Also, in cases such as when the arm unit 120 is remote-controlled, the detection of operating input may also be conducted by the operation input unit 1300.

In step S10, if it is determined that operating input of at least a fixed value has been detected, the flow proceeds to step S12, and the enlargement factor of an image captured by the camera 1200 is acquired. Specifically, the central processing unit 1100 acquires the zoom factor from the camera 1200, and acquires the enlargement factor from the zoom factor and distance information about the subject.

In the following step S14, the viscosity, the velocity, or the amount of movement according to the enlargement factor is calculated. As discussed above, the viscosity, the velocity, and the amount of movement according to the enlargement factor may be computed from a map prescribing a relationship between the enlargement factor and these parameters.

In the next step S16, driving of the arm unit 120 by force control is started. At this point, since the viscosity, the velocity, or the amount of movement is controlled according to the enlargement factor, fine adjustment of the arm unit becomes possible to the extent that the enlargement factor is high. After step S16, the flow returns to step S10.

Meanwhile, in the case of determining in step S10 that operating input of at least a fixed value has not been detected, the flow proceeds to step S18. In step S18, control locking the orientation of the arm unit 120 to the current orientation is performed.

Figure 10:
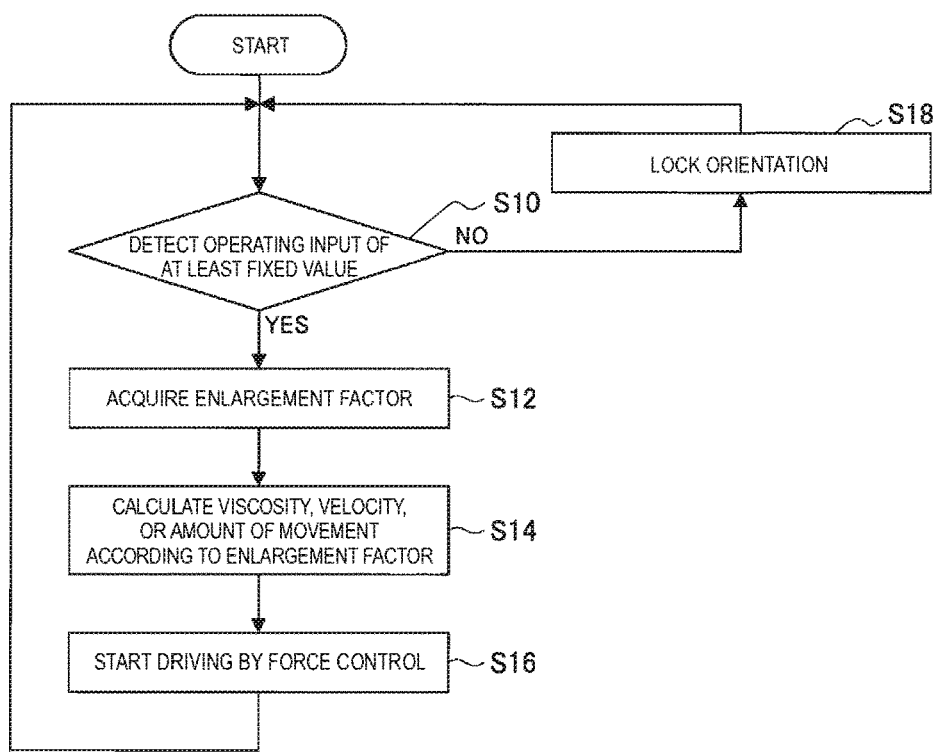
FIG. 10 is a flowchart illustrating a process of control according to a zoom factor.

As above, according to the process in FIG. 10, if operating input of at least a fixed value is detected, the viscosity, the movement velocity of the arm, or the amount of movement of the arm is controlled according to the enlargement factor. Consequently, if the enlargement factor is large, it becomes possible to increase the viscosity. Also, if the enlargement factor is large, control that decreases the movement velocity or the amount of movement of the arm becomes possible. Consequently, if the enlargement factor is high, it becomes possible to make more precise fine adjustments of the arm unit.

Next, control of the viscosity of the driving of a joint unit based on the state of the joint unit will be described. As discussed above, in the robot arm control method according to the present embodiment, the state of the joint unit 130 is detected. Subsequently, based on the state of the joint unit 130, the arm state is acquired by the arm state acquiring unit 241. The arm state refers to the state of motion of the arm unit 120, and may be properties such as the position, the velocity, and the acceleration of each structural member of the arm unit 120, or the force acting on each structural member of the arm unit 120, for example.

The central processing unit 1100 controls the viscosity of the driving of the joint unit 130 based on the state of the joint unit 130. For example, if the arm unit 120 moves in a certain predetermined direction, control is performed to raise the viscosity or lower the viscosity compared to normal. Also, if the arm unit 120 is in a certain predetermined orientation, control is performed to raise the viscosity or lower the viscosity compared to normal. Also, if the arm unit 120 moves at a certain predetermined velocity, control is performed to raise the viscosity or lower the viscosity compared to normal.

In the central processing unit 1100, the arm state acquiring unit 241 acquires the state of the joint unit 130 (arm state). The operation condition setting unit 242 computes the value of viscosity according to the state of the joint unit 130 as the purpose of motion discussed earlier. Additionally, the processes discussed earlier are performed by the virtual force calculating unit 243 and the actual force calculating unit 244, a process is performed by the ideal joint control unit 250, and in addition, a torque command value τ is computed based on the computed value of viscosity, and sent to each of the motor control units 1500a, 1500b, . . . , 1500c. The motor control units 1500a, 1500b, . . . , 1500f respectively control the motors 1700a, 1700b, . . . , 1700f based on the torque command value τ. As discussed earlier, the motor driver 425 of the robot arm apparatus 10 is able to adjust a viscous drag coefficient on rotary motion of the actuator 430 by adjusting the amount of current supplied to the motor 424.

Consequently, since the viscosity changes according to the direction, the orientation, and the velocity of the motion of the arm unit 120, the motion of the arm unit 120 may be made lighter or heavier in the case of motion in a certain direction or a certain orientation, and optimal motion according to the operator's needs may be realized. More specifically, by changing the viscosity in a specific direction based on position information obtained from the state of the joint unit 130, it is possible to make fine adjustments in just a specific direction easier to perform. For example, by raising the viscosity with respect to the XY directions displayed on a screen, and making the viscosity heavier with respect to the Z direction, it is possible to make operations only in the XY directions easier to perform while also limiting motion in a specific direction. Additionally, based on velocity information obtained from the state of the joint unit 130, by switching so as to lower the viscosity and make movement easier when at least a certain speed is reached, the operator becomes able to select between the operability of fine movement and large motion. Additionally, by adjusting the viscosity based on acceleration information obtained from the state of the joint unit 130, it is possible to move at a fixed velocity without being influenced by the uneven application of manual force, thereby making it easier to observe an affected area without requiring delicate and even application of force. Additionally, by raising the viscosity to limit motion in the direction proceeding towards an affected area of the patient based on position information obtained from the state of the joint unit 130, it becomes possible to allow operations in other directions while increasing safety.

Control of the viscosity based on the state of the joint unit 130 and control of the viscosity based on the enlargement factor discussed earlier may also be conducted in combination with each other. In this case, the central processing unit 1100 controls the viscosity of the driving of the joint unit 130 based on the state of the joint unit 130 and the enlargement factor.

<5. Operation Matching on-screen Directions>

Next, a technique of operating the arm unit 120 to match on-screen X Y directions according to the present embodiment will be described. According to the robot arm apparatus 10 according to the present embodiment, if the joint unit 421f is rotationally driven, the subject may be rotated with respect to the display screen of the display device 30.

FIG. 11(A) illustrates the positional relationship between the subject and the frame 30a of the display device 30 before the joint unit 421f is rotationally driven. Also, FIG. 11(B) illustrates the positional relationship between the subject and the frame 30a of the display device 30 after the joint unit 421f is rotated. By causing the joint unit 421f to rotated from the state in FIG. 11(A) to the state in FIG. 11(B), the frame 30a of the display device 30 rotates clockwise with respect to the subject. In other words, the subject rotates counter-clockwise with respect to the frame 30a of the display device 30.

On the other hand, suppose that while the joint unit 421f rotates, the joint units other than the joint unit 421f are not operating. At this point, suppose a case in which, from the state in FIG. 11(B), the user operates the operation input unit 1300, and moves the arm unit 120 by remote control. In the case of operating the arm in the Y axis direction in FIG. 11(B), if the robot arm apparatus 10 does not account for the rotation of the display frame 30a from FIG. 11(A) to FIG. 11(B), the robot arm apparatus 10 will recognize the operation as being performed in the Y axis direction illustrated in FIG. 11(A). For this reason, the display frame 30a moves in the Y' axis direction in FIG. 11(B). Consequently, the direction in which the operator is attempting to move the arm unit 120 on the display screen becomes different from the actual movement direction of the arm unit 120, which feels unnatural to the operator who is performing operations while looking at the display screen, and also reduces operability.

Figure 11:
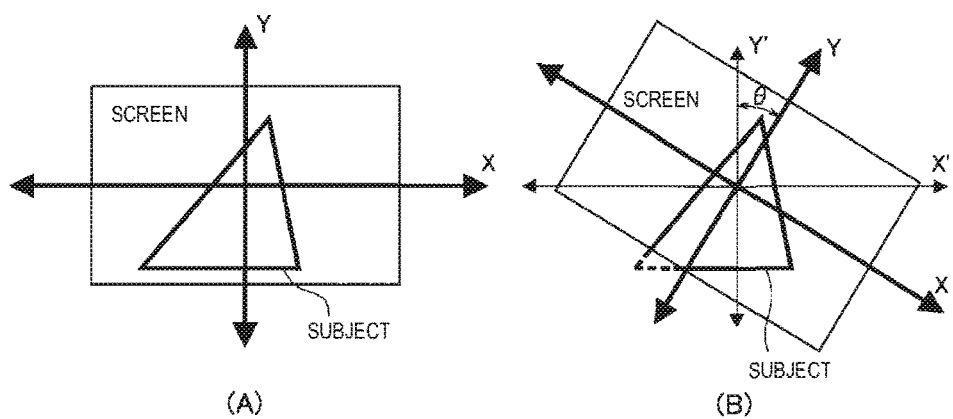
FIG. 11 is a schematic diagram for describing operation of a robot arm that matches on-screen directions.

For this reason, in the present embodiment, a process that realizes arm motion matching the on-screen directions is conducted. Specifically, the angular position of the camera 1200 with respect to the subject is acquired, and when the angular position of the camera 1200 with respect to the subject changes, the operation direction is corrected while accounting for the magnitude of the change. In the example of FIG. 11, when transitioning from FIG. 11(A) to FIG. 11(B), the camera 1200 rotates by an angle θ, and the subject rotates by the angle θ with respect to the frame 30*a* of the display screen. Thus, for an operation direction input by the user, the direction in which the arm unit 120 is to move is corrected by the angle θ. Consequently, when the user performs an operation in the Y axis direction in FIG. 11(B), the arm unit 120 moves in the Y axis direction, and thus the direction in which the arm unit 120 moves matches the operation direction on the display screen, thereby making it possible to increase operability greatly.

Figure 12:
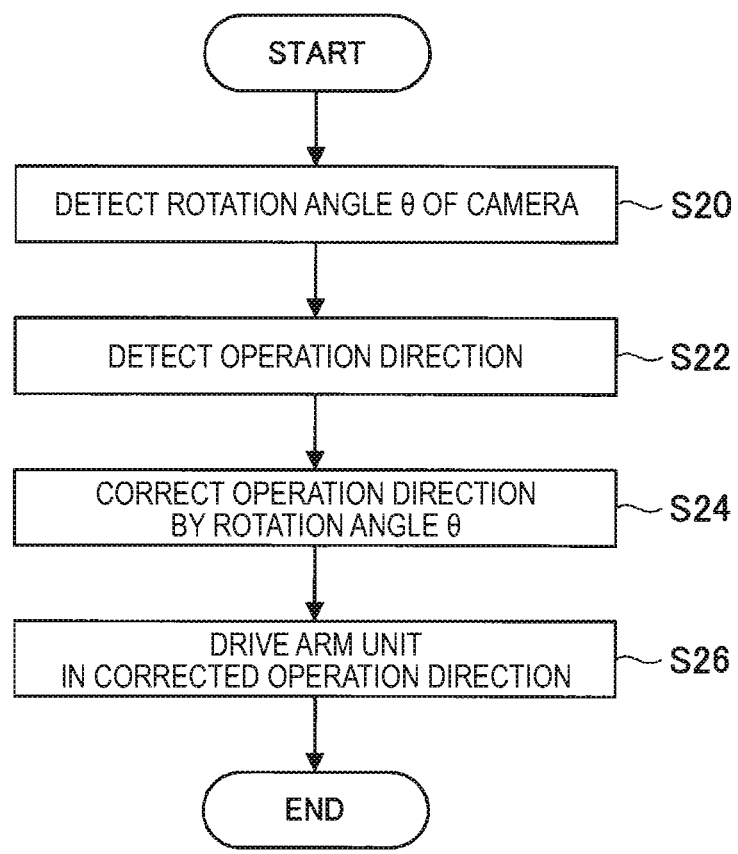
FIG. 12 is a flowchart illustrating a process of operating an arm unit to match the on-screen XY directions illustrated in FIG. 11.

FIG. 12 is a flowchart illustrating a process of operating the arm unit to match the on-screen XY directions illustrated in FIG. 11. First, in step S20, the rotation angle θ of the camera 1200 is detected. At this point, the angle θ illustrated in FIG. 11(B) is computed. The angle θ may be computed from the encoder 1600*f* of the joint unit 421*f*.

In the following step S22, an operation direction input into the operation input unit 1300 by the user is detected. As described using FIG. 11(B), even if the user performs an operation in the Y axis direction on the screen in FIG. 11(B), the robot arm apparatus 10 recognizes the operation as an operation in the Y' axis direction.

In the following step S24, the operation direction input into the operation input unit 1300 by the user is corrected by the angle θ. As a result, in FIG. 11(B), the operation direction is corrected from the Y' axis direction to the Y axis direction. In the following step S26, the arm unit 120 is driven in the corrected operation direction.

As above, by deciding the operation direction while accounting for the rotation angle θ of the camera 1200, it becomes possible to make the operation direction specified on-screen by the user match the actual operation direction of the arm unit 120. Consequently, the user becomes able to perform operations intuitively while looking at the screen, making it possible to greatly improve operability.

<6. Hardware Configuration>

Figure 13:
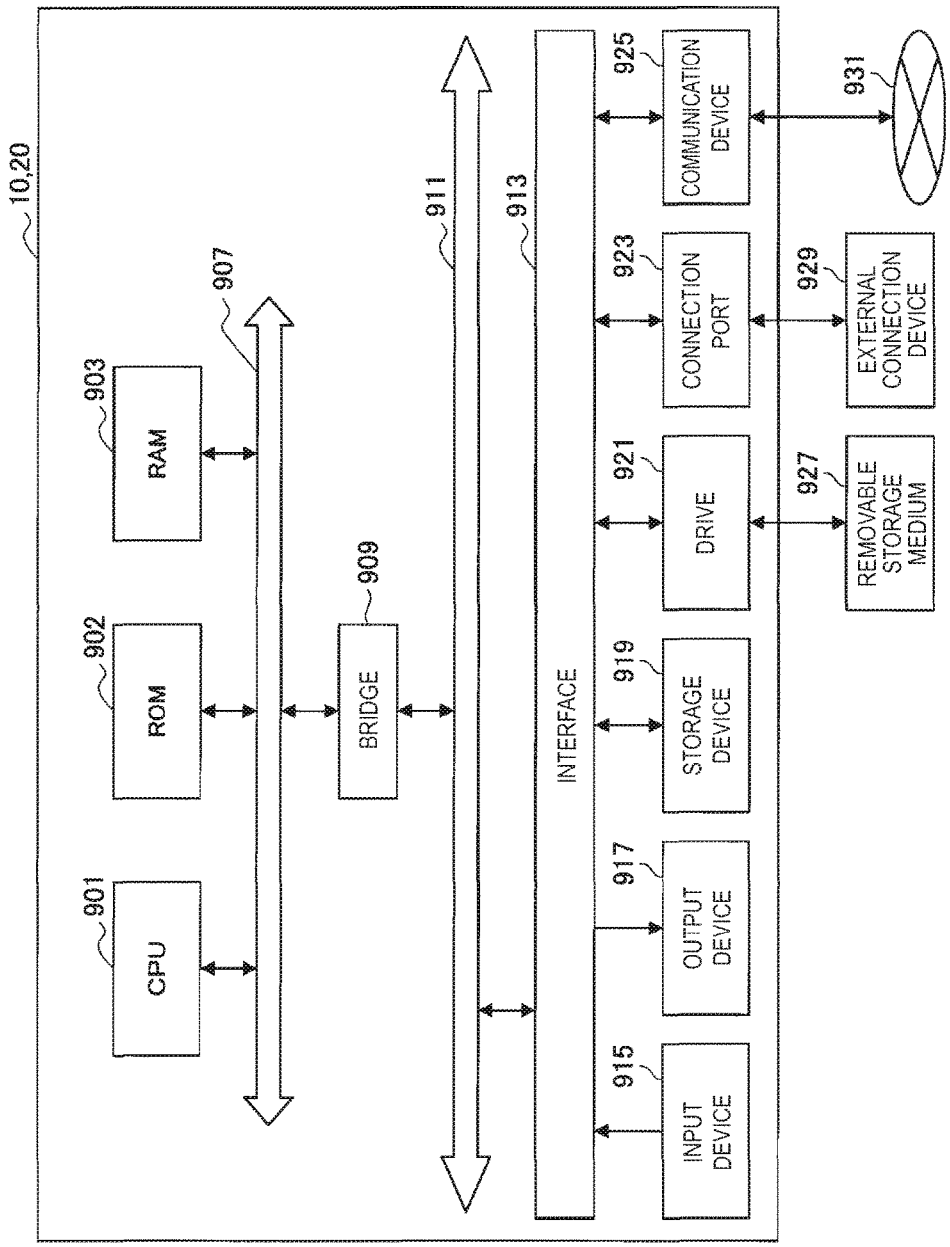
FIG. 13 is a functional block diagram illustrating an exemplary configuration of a hardware configuration of a robot arm apparatus and a control device according to an embodiment of the present disclosure.

Next, a hardware configuration of the robot arm apparatus 10 and the control device 20 according to the present embodiment illustrated in FIG. 6 will be described in detail with reference to FIG. 13. FIG. 13 is a functional block diagram illustrating an exemplary configuration of a hardware configuration of the robot arm apparatus 10 and the control device 20 according to an embodiment of the present disclosure.

The robot arm apparatus 10 and the control device 20 mainly include a CPU 901, a ROM 903, and a RAM 905. The robot arm apparatus 10 and the co device 20 further include a host bus 907, a bridge 909, an external bus 911, an interface 913, an input device 915, an output device 917, a storage device 919, a drive 921, a connection port 923, and a communication device 925.

The CPU 901 functions as an arithmetic processing device and a control device, and controls all or some operations of the robot arm apparatus 10 and the control device 20 according to various kinds of programs recorded in the ROM 903, the RAM 905, the storage device 919, or a removable storage medium 927. The ROM 903 stores a program, an operation parameter, or the like used by the CPU 901. The RAM 905 primarily stores a program used by the CPU 901, a parameter that appropriately changes in execution of a program, or the like. The above-mentioned components are connected with one another by the host bus 907 configured with an internal bus such as a CPU bus. The CPU 901 corresponds to, for example, 6 the arm control unit 110 and the control unit 230 illustrated in FIG. 6 in the present embodiment.

The host bus 907 is connected to the external bus 911 such as a peripheral component interconnect/interface (PCI) bus through the bridge 909. Further, the input device 915, the output device 917, the storage device 919, the drive 921, the connection port 923, and the communication device 925 are connected to the external bus 911 via the interface 913.

The input device 915 is an operating unit used by the user such as a mouse, a keyboard, a touch panel, a button, a switch, a lever, or a pedal. For example, the input device 915 may be a remote control unit (a so-called remote controller) using infrared light or any other radio waves, and may be an external connection device 929 such as a mobile telephone or a PDA corresponding to an operation of the robot arm apparatus 10 and the control device 20. Further, for example, the input device 915 is configured with an input control circuit that generates an input signal based on information input by the user using the operating unit, and outputs the input signal to the CPU 901. The user of the robot arm apparatus 10 and the control device 20 can input various kinds of data to the robot arm apparatus 10 and the control device 20 or instruct the robot arm apparatus 10 and the control device 20 to perform a processing operation by operating the input device 915. For example, the input device 915 corresponds to the input unit 210 illustrated in FIG. 6 in the present embodiment. Further, in the present embodiment, the purpose of motion in driving of the arm unit 120 may be set by an operation input through the input device 915 by the user, and the whole body cooperative control may be performed according to the purpose of motion.

The output device 917 is configured with a device capable of visually or acoustically notifying the user of the acquired information. As such a device, there are a display device such as a CRT display device, a liquid crystal display device, a plasma display device, an EL display device or a lamp, an audio output device such as a speaker or a headphone, a printer device, and the like. For example, the output device 917 outputs a result obtained by various kinds of processes performed by the robot arm apparatus 10 and the control device 20. Specifically, the display device displays a result obtained by various kinds of processes performed by the robot arm apparatus 10 and the control device 20 in the form of text or an image. Meanwhile, the audio output device converts an audio signal including reproduced audio data, acoustic data, or the like into an analogue signal, and outputs the analogue signal. In the present embodiment, various kinds of information related to driving control of the arm unit 120 may be output from the output device 917 in all forms. For example, in driving control of the arm unit 120, the trajectory of movement of each component of the arm unit 120 may be displayed on the display screen of the output device 917 in the form of a graph. Further, for example, the display device 30 illustrated in FIG. 6 may be a device including the function and configuration of the output device 917 serving as the display device and a component such as a control unit for controlling driving of the display device.

The storage device 919 is a data storage device configured as an exemplary storage unit of the robot arm apparatus 10 and the control device 20. For example, the storage device 919 is configured with a magnetic storage unit device such as a hard disk drive (HDD), a semiconductor storage device, an optical storage device, a magneto optical storage device, or the like. The storage device 919 stores a program executed by the CPU 901, various kinds of data, and the like. For example, the storage device 919 corresponds to the storage unit 220 illustrated in FIG. 6 in the present embodiment. Further, in the present embodiment, the storage device 919 may store the operation condition (the purpose of motion and the constraint condition) in the operation related to the whole body cooperative control using the generalized inverse dynamics, and the robot arm apparatus 10 and the control device 20 may perform the operation related to the whole body cooperative control using the operation condition stored in the storage device 919.

The drive 921 is a recording medium reader/writer, and is equipped in or attached to the robot arm apparatus 10 and the control device 20. The drive 921 reads information stored in the removable storage medium 927 mounted thereon such as a magnetic disk, an optical disc, a magneto optical disc, or a semiconductor memory, and outputs the read information to the RAM 905. Further, the drive 921 can write a record in the removable storage medium 927 mounted thereon such as a magnetic disk, an optical disk, a magneto optical disk, or a semiconductor memory. For example, the removable storage medium 927 is a DVD medium, an HD-DVD medium, a Blu-ray (a registered trademark) medium, or the like. Further, the removable storage medium 927 may be a Compact Flash (CF) (a registered trademark), a flash memory, a Secure Digital (SD) memory card, or the like. Furthermore, for example, the removable storage medium 927 may be an integrated circuit (IC) card equipped with a non-contact type IC chip, an electronic device, or the like. In the present embodiment, various kinds of information related to driving control of the arm unit 120 is read from various kinds of removable storage media 927 or written in various kinds of removable storage media 927 through the drive 921.

The connection port 923 is a port for connecting a device directly with the robot arm apparatus 10 and the control device 20. As an example of the connection port 923, there are a Universal Serial Bus (USB) port, an IEEE1394 port, a Small Computer System Interface (SCSI) port, and the like. As another example of the connection port 923, there are an RS-232C port, an optical audio terminal, a High-Definition Multimedia Interface (HDMI) (a registered trademark), and the like. As the external connection device 929 is connected to the connection port 923, the robot arm apparatus 10 and the control device 20 acquire various kinds of data directly from the external connection device 929 or provide various kinds of data to the external connection device 929. In the present embodiment, various kinds of information related to driving control of the arm unit 120 may be read from various kinds of external connection devices 929 or written in various kinds of external connection devices 929 through the connection port 923.

For example, the communication device 925 is a communication interface configured with a communication device used for a connection with a communication network (network) 931. For example, the communication device 925 is a communication card for a wired or wireless local area network (LAN), Bluetooth (a registered trademark), or wireless USB (WUSB). Further, the communication device 925 may be an optical communication router, an asymmetric digital subscriber line (ADSL) router, various kinds of communication modems, or the like. For example, the communication device 925 can transmit or receive a signal to or from the Internet or another communication device, for example, according to a certain protocol such as TCP/IP. Further, the communication network 931 connected to the communication device 925 is configured with a network connected in a wired or wireless manner, and may be, for example, the Internet, a domestic LAN, infrared ray communication, radio wave communication, satellite communication, or the like. In the present embodiment, various kinds of information related to driving control of the arm unit 120 may be transmitted or received to or from an external device via the communication network 931 through the communication device 925.

The hardware configuration capable of implementing the functions of the robot arm apparatus 10 and the control device 20 according to an embodiment of the present disclosure has been described above. Each of the above components may be configured using a versatile member, and may be configured by hardware specialized for the function of each component. Thus, the hardware configuration to be used may be appropriately changed according to a technology level when the present embodiment is carried out. Further, although not illustrated in FIG. 13, the robot arm apparatus 10 obviously includes various kinds of components corresponding to the arm unit 120 illustrated in FIG. 6, Further, it is possible to create a computer program for implementing the functions of the robot arm apparatus 10 according to the present embodiment, the control device 20, and the display device 30 and install the computer program in a personal computer or the like. Furthermore, it is possible to provide a computer readable recording medium storing the computer program as well. Examples of the recording medium include a magnetic disk, an optical disc, a magneto optical disc, and a flash memory. Further, for example, the computer program may be delivered via a network without using the recording medium.

The virtual force calculating unit 243 calculates virtual force in the operation related to the whole body cooperative control using the generalized inverse dynamics. For example, a virtual force calculation process performed by the virtual force calculating unit 243 may be a series of processes described above in (5-2-2-1. Virtual force calculating process). The virtual force calculating unit 243 transmits the calculated virtual force $f_v$ to the actual force calculating unit 244.

The actual force calculating unit 244 calculates actual force in the operation related to the whole body cooperative control using the generalized inverse dynamics. For example, an actual force calculation process performed by the actual force calculating unit 244 may be a series of processes described above in (5-2-2-2. Actual force calculating process). The actual force calculating unit 244 transmits the calculated actual force (the generated torque) $\tau_a$ to the ideal joint control unit 250. Further, in the present embodiment, the generated torque $\tau_a$ calculated by the actual force calculating unit 244 is also referred to as a "control value" or a "control torque value" to mean a control value of the joint unit 130 in the whole body cooperative control.

The ideal joint control unit 250 performs various kinds of operations related to the ideal joint control for implementing the ideal response based on the theoretical model. In the present embodiment, the ideal joint control unit 250 corrects influence of a disturbance on the generated torque $\tau_a$ calculated by the actual force calculating unit 244, and calculates the torque command value τ for implementing the ideal response of the arm unit 120. The operation process performed by the ideal joint control unit 250 corresponds to a series of processes described above in (5-2-3. Ideal joint control).

The ideal joint control unit 250 includes a disturbance estimating unit 251 and a command value calculating unit 252.

The disturbance estimating unit 251 calculates the disturbance estimation value $\tau_d$ based on the torque command value τ and the rotational angular velocity calculated from the rotational angle q detected by the rotational angle detecting unit 133. Here, the torque command value τ refers to the command value indicating the generated torque of the arm unit 120 that is finally transmitted to the robot arm apparatus 10. As described above, the disturbance estimating unit 251 has a function corresponding to the disturbance observer 620 illustrated in FIG. 8.

The command value calculating unit 252 calculates the torque command value τ serving as the command value indicating torque that is generated by the arm unit 120 and finally transmitted to the robot arm apparatus 10 using the disturbance estimation value $\tau_d$ calculated by the disturbance estimating unit 251. Specifically, the command value calculating unit 252 calculates the torque command value τ by adding the disturbance estimation value $\tau_d$ calculated by the disturbance estimating unit 251 to $\tau^{ref}$ calculated from the ideal model of the joint unit 130 expressed by Equation (12). For example, when the disturbance estimation value $\tau_d$ is not calculated, the torque command value τ is used as the torque target value $\tau^{ref}$. As described above, the function of the command value calculating unit 252 corresponds to a function other than that of the disturbance observer 620 illustrated in FIG. 8.

As described above, in the ideal joint control unit 250, a series of processes described above with reference to FIG. 8 is performed such that information is repeatedly exchanged between the disturbance estimating unit 251 and the command value calculating unit 252. The ideal joint control unit 250 transmits the calculated torque command value τ to the drive control unit 111 of the robot arm apparatus 10. The drive control unit 111 performs control of supplying an amount of electric current corresponding to the transmitted torque command value τ to the motor in the actuator of the joint unit 130, controls the number of revolutions of the motor, and controls the rotational angle and the generated torque of the joint unit 130.

Furthermore, according to the present embodiment, since the respective 1800a, 1800b, . . . , 1800f in the joint units are able to detect user operations, it becomes possible to move the arm unit 120 by operating any part of the arm unit 120 of the robot arm apparatus 10. Consequently, it becomes possible to move the arm unit 120 without holding the arm unit 120 in one's hand, such as with an operation of pushing the arm unit 120 with one's arm or the like.

In addition, by causing each joint unit to produce a viscosity suited to the enlargement factor (enlargement ratio) of the display device 30, it becomes possible to raise the viscosity when the enlargement factor is high to make fine adjustments easier to perform, or lower the viscosity when the enlargement factor is low to make the arm unit easier to move. Consequently, by causing the actual amount of movement of the arm unit 120 to match the operator's intuitively perceived amount of force, an intuitive opposing force may be returned from the arm unit 120 to the operator even during work performed while looking at only a wide field of view on the display device 30, thereby making it possible to greatly improve operability.

Note that although the foregoing embodiment illustrates an example of applying the present disclosure to a robot arm apparatus for medical use, the present disclosure is applicable to robot arm apparatuses for a variety of applications other than medical use.

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

For example, the above embodiment has shown an example in which a front edge unit of an arm unit of a robot arm apparatus is an imaging unit, and a medical procedure part is photographed by the imaging unit during surgery as illustrated in FIG. 1, but the present embodiment is not limited to this example. The robot arm control system 1 according to the present embodiment can be applied even when a robot arm apparatus including a different front edge unit is used for another purpose. For example, the front edge unit may be an endoscope or a laparoscope, and may be any other examination device such as an ultrasonic examination apparatus or a gastrocamera.

For example, in a medical procedure using a laparoscope, the laparoscope is operated with the robot arm to insert the laparoscope inside the patient's body, and treatment is performed by using forceps and an electrosurgical instrument inserted inside the patient's body while observing a picture of the site of the medical procedure on a monitor by operating the laparoscope. With such a medical procedure method, if the practitioner were able to operate the forceps and the electrosurgical instrument while operating the laparoscope for observing the site of the medical procedure with the robot arm, for example, it would be possible for a single person to perform the medical procedure, enabling more efficient medical procedures. However, with typical existing balance arms, from the perspective of operability, it is difficult for a single person to operate the forceps and the electrosurgical instrument by hand and operate the laparoscope with the robot arm simultaneously. Thus, existing methods require multiple staff members, and it is typical to have one practitioner perform the procedure while operating the laparoscope, while another practitioner operates the forceps and the electrosurgical instrument. However, with a robot arm apparatus according to the present embodiment, high operability by whole body cooperative control is realized, as discussed above. In addition, by ideal joint control, high-precision response and high stability with fewer effects such as vibration are realized. Consequently, by operating a laparoscope for observation with a robot arm apparatus according to the present embodiment, for example, operation of the forceps and the electrosurgical instrument for the procedure by hand and operation of the laparoscope for observation by the robot arm apparatus may be performed easily by a single practitioner.

Further, the robot arm apparatus according to the present embodiment may be used for purposes other than medical uses. In the robot arm apparatus according to the present embodiment, since the high-accuracy responsiveness and the high stability are implemented through the ideal joint control, for example, it is also possible to deal with a task such as processing or assembly of industrial components that has to be performed with a high degree of accuracy.

Further, the above embodiment has been described in connection with the example in which the joint unit of the robot arm apparatus includes a rotation mechanism, and rotary driving of the rotation mechanism is controlled such that driving of the arm unit is controlled, but the present embodiment is not limited to this example. For example, in the robot arm apparatus according to the present embodiment, the link configuring the arm unit may have a mechanism that expands or contracts in an extension direction of the link, and the length of the link may be variable. When the length of the link is variable, for example, driving of the arm unit is controlled such that a desired purpose of motion is achieved by the whole body cooperative control in which expansion and contraction of the link is considered in addition to rotation in the joint unit.

Further, the above embodiment has been described in connection with the example in which the degrees of freedom of the arm unit in the robot arm apparatus are the 6 or more degrees of freedom, but the present embodiment is not limited to this example. Further, the description has proceeded with the example in which each of the plurality of joint units configuring the arm unit includes the actuator that supports the ideal joint control, but the present embodiment is not limited to this example. In the present embodiment, various purposes of motion can be set according to the purpose of the robot arm apparatus. Thus, as long as the set purpose of motion can be achieved, the arm unit may have fewer than 6 degrees of freedom, and some of the plurality of joint units configuring the arm unit may be joint units having a general joint mechanism. As described above, in the present embodiment, the arm unit may be configured to be able to achieve the purpose of motion or may be appropriately configured according to the purpose of the robot arm apparatus.

Additionally, the present technology may also be configured as below.

(1)
A robot arm apparatus, including:
one or a plurality of a joint unit that joins a plurality of links constituting a multi-link structure;
an acquisition unit that acquires an enlargement factor of an image imaged by an imaging unit attached to the multi-link structure; and
a driving control unit that controls driving of the joint unit based on a state of the joint unit and the enlargement factor.

(2)
The robot arm apparatus according to (1), wherein
the driving control unit controls a viscosity of driving of the joint unit according to the enlargement factor.

(3)
The robot arm apparatus according to (2), wherein
the driving control unit raises the viscosity of driving of the joint unit as the enlargement factor increases.

(4)
The robot arm apparatus according to (2), wherein
the driving control unit selects a characteristic from a plurality of characteristics prescribing a relationship between the enlargement factor and the viscosity of driving of the joint unit, and controls the viscosity of driving of the joint unit based on the selected characteristic.

(5)
The robot arm apparatus according to (1), wherein
the driving control unit controls a driving velocity of the joint unit according to the enlargement factor.

(6)
The robot arm apparatus according to (5), wherein
the driving control unit lowers the driving velocity of the joint unit as the enlargement factor increases.

(7)
The robot arm apparatus according to (1), wherein
the driving control unit controls a driving magnitude of the joint unit according to the enlargement factor.

(8)
The robot arm apparatus according to (7), wherein
the driving control unit decreases the driving magnitude of the joint unit with respect to an operation, as the enlargement factor increases.

(9)
The robot arm apparatus according to any one of (1) to (8), wherein
the driving control unit controls driving of the joint unit based on the state of the joint unit and a zoom factor by the imaging unit.

(10)
The robot arm apparatus according to (1), wherein
the enlargement factor is computed from a zoom factor by the imaging unit and distance information about the subject.

(11)
The robot arm apparatus according to any one of (1) to (10), further including:
a detecting unit that detects an operating input by an operator, wherein
the driving control unit controls driving of the joint unit when the operating input is detected.

(12)
The robot arm apparatus according to (11), wherein
the detecting unit detects an external force acting on the multi-link structure as the operating input.

(13)
The robot arm apparatus according to (1), wherein
each of a plurality of the joint unit includes a joint state detecting unit that detects a state of the joint unit, and
the joint state detecting unit at least includes
a torque detecting unit that detects a generated torque in the joint unit and an external torque applied from an outside to the joint unit, and
a rotational angle detecting unit that detects a rotational angle of the joint unit.

(14)
The robot arm apparatus according to (13), wherein
a control value and a command value are the generated torque in the joint unit.

(15)
The robot arm apparatus according to (1), wherein
the driving control unit controls driving of the joint unit based on a control value for whole body cooperative control of the multi-link structure computed by generalized inverse dynamics using a state of the multi-link structure acquired based on a plurality of detected states of the joint unit, and a purpose of motion and a constraint condition of the multi-link structure.

(16)
The robot arm apparatus according to (15), wherein
the control value is computed based on a virtual force which is an imaginary force acting to achieve the purpose of motion in an operation space describing a relationship between a force acting on the multi-link structure and an acceleration produced in the multi-link structure, and also based on an actual force computed by converting the virtual force into a real force for driving the joint unit based on the constraint condition.

(17)
The robot arm apparatus according to (15), wherein the driving control unit controls driving of the joint unit based on a command value computed by correcting influence of a disturbance on the control value.

(18)
The robot arm apparatus according to (17), wherein the command value is computed by correcting the control value using a disturbance estimation value expressing influence of a disturbance on driving of the joint unit estimated based on a detected state of the joint unit.

(19)
The robot arm apparatus according to (15), wherein the purpose of motion is an action that at least controls the state of the joint unit so as to cancel out gravity acting on the multi-link structure, and also controls the state of the joint unit so as to support movement of the multi-link structure in a direction of force applied additionally from an outside.

(20)
The robot arm apparatus according to any one of (1) to (16), wherein the robot arm apparatus is an apparatus for medical use.

(21)
A program causing a computer to function as:
means for detecting a state of one or a plurality of a joint unit that joins a plurality of links constituting a multi-link structure;
means for acquiring an on-screen enlargement factor of a subject imaged by an imaging unit attached to the multi-link structure; and
means for controlling driving of the joint unit based on a state of the joint unit and the enlargement factor.

(22)
A robot arm apparatus, including:
one or a plurality of a joint unit that joins a plurality of links constituting a multi-link structure; and
a driving control unit that controls a viscosity of driving of the joint unit based on a state of the joint unit.

(23)
The robot arm apparatus according to (22), further including:
an acquisition unit that acquires an on-screen enlargement factor of a subject imaged by an imaging unit attached to the multi-link structure, wherein
the driving control unit controls a viscosity of driving of the joint unit according to the enlargement factor.

(24)
The robot arm apparatus according to (23), wherein the driving control unit raises the viscosity of driving of the joint unit as the enlargement factor increases.

(25)
The robot arm apparatus according to (23), wherein the driving control unit selects a characteristic from a plurality of characteristics prescribing a relationship between the enlargement factor and the viscosity of driving of the joint unit, and controls the viscosity of driving of the joint unit based on the selected characteristic.

(26)
The robot arm apparatus according to (22) to (25), wherein the robot arm apparatus is an apparatus for medical use.

(27)
The robot arm apparatus according to (22), wherein the state of the joint unit is an orientation of the multi-link structure.

(28)
The robot arm apparatus according to (22), wherein the state of the joint unit is a driving velocity of the joint unit.

(29)
The robot arm apparatus according to (22), wherein the state of the joint unit is a driving direction of the joint unit.

(30)
A robot arm apparatus control method, including:
detecting one or a plurality of a state of one or a plurality of a joint unit that joins a plurality of links constituting a multi-link structure;
acquiring an on-screen enlargement factor of a subject imaged by an imaging unit attached to the multi-link structure; and
controlling driving of the joint unit based on a state of the joint unit and the enlargement factor.

REFERENCE SIGNS LIST 1 robot arm control system
10 robot arm apparatus
20 control device
30 display device
110 arm control unit
111 drive control unit
120 arm unit
130 joint unit
131 joint driving unit
132 rotational angle detecting unit
133 torque detecting unit
140 imaging unit
210 input unit
220 storage unit
230 control unit
240 whole body cooperative control unit
241 arm state acquiring unit
242 operation condition setting unit
243 virtual force calculating unit
244 actual force calculating unit
250 ideal joint control unit
251 disturbance estimating unit
252 command value calculating unit

The invention claimed is:
1. A robot arm apparatus, comprising:
one or a plurality of a joint unit that joins a plurality of links constituting a multi-link structure;
processing circuitry configured to:
acquire an on-screen enlargement factor of a subject imaged by an imaging unit attached to the multi-link structure; and
control driving of the joint unit based on a state of the joint unit and the enlargement factor,
wherein the processing circuitry controls a viscosity of driving of the joint unit according to the state of the joint unit and the enlargement factor, and
wherein the processing circuitry lowers a driving velocity of the joint unit as the enlargement factor increases.

2. The robot arm apparatus according to claim 1, wherein the processing circuitry raises the viscosity of driving of the joint unit as the enlargement factor increases.

3. The robot arm apparatus according to claim 1, wherein the processing circuitry selects a characteristic from a plurality of characteristics prescribing a relationship between the enlargement factor and the viscosity of driving of the joint unit, and controls the viscosity of driving of the joint unit based on the selected characteristic.

4. The robot arm apparatus according to claim 1, wherein the processing circuitry controls a driving magnitude of the joint unit according to the enlargement factor.

5. The robot arm apparatus according to claim 4, wherein the processing circuitry decreases the driving magnitude of the joint unit with respect to an operation, as the enlargement factor increases.

6. The robot arm apparatus according to claim 1, wherein the processing circuitry controls driving of the joint unit based on the state of the joint unit and a zoom factor by the imaging unit.

7. The robot arm apparatus according to claim 1, wherein the enlargement factor is computed from a zoom factor by the imaging unit and distance information about the subject.

8. The robot arm apparatus according to claim 1, wherein the processing circuitry further configured to:
   detect an operating input by an operator, wherein the processing circuitry controls driving of the joint unit when the operating input is detected.

9. The robot arm apparatus according to claim 8, wherein the processing circuitry detects an external force acting on the multi-link structure as the operating input.

10. The robot arm apparatus according to claim 1, wherein each of a plurality of the joint unit includes a joint state detecting unit that detects a state of the joint unit, and
   the joint state detecting unit at least includes:
      a torque detecting unit that detects a generated torque in the joint unit and an external torque applied from an outside to the joint unit, and
      a rotational angle detecting unit that detects a rotational angle of the joint unit.

11. The robot arm apparatus according to claim 10, wherein a control value and a command value are the generated torque in the joint unit.

12. The robot arm apparatus according to claim 1, wherein the processing circuitry controls driving of the joint unit based on a control value for whole body cooperative control of the multi-link structure computed by generalized inverse dynamics using a state of the multi-link structure acquired based on a plurality of detected states of the joint unit, and a purpose of motion and a constraint condition of the multi-link structure.

13. The robot arm apparatus according to claim 12, wherein the control value is computed based on a virtual force which is an imaginary force acting to achieve the purpose of motion in an operation space describing a relationship between a force acting on the multi-link structure and an acceleration produced in the multi-link structure, and also based on an actual force computed by converting the virtual force into a real force for driving the joint unit based on the constraint condition.

14. The robot arm apparatus according to claim 12, wherein the processing circuitry controls driving of the joint unit based on a command value computed by correcting influence of a disturbance on the control value.

15. The robot arm apparatus according to claim 14, wherein the command value is computed by correcting the control value using a disturbance estimation value expressing influence of a disturbance on driving of the joint unit estimated based on a detected state of the joint unit.

16. The robot arm apparatus according to claim 12, wherein the purpose of motion is an action that at least controls the state of the joint unit so as to cancel out gravity acting on the multi-link structure, and also controls the state of the joint unit so as to support movement of the multi-link structure in a direction of force applied additionally from an outside.

17. The robot arm apparatus according to claim 1, wherein the robot arm apparatus is an apparatus for medical use.

18. A non-transitory computer readable medium storing a program causing a computer to:
   detect a state of one or a plurality of a joint unit that joins a plurality of links constituting a multi-link structure;
   acquire an on-screen enlargement factor of a subject imaged by an imaging unit attached to the multi-link structure: and
   control driving of the joint unit based on a state of the joint unit and the enlargement factor,
   wherein a viscosity of driving of the joint unit is controlled according to the state of the joint unit and the enlargement factor, and
   wherein a driving velocity of the joint unit is lowered as the enlargement factor increases.

19. A robot arm apparatus, comprising:
   one or a plurality of a joint unit that joins a plurality of links constituting a multi-link structure; and
   processing circuitry configured to:
      control a viscosity of driving of the joint unit based on a state of the joint unit, and
      acquire an on-screen enlargement factor of a subject imaged by an imaging unit attached to the multi-link structure,
   wherein the processing circuitry controls a viscosity of driving of the joint unit according to the enlargement factor, and
   wherein a driving velocity of the joint unit is lowered as the enlargement factor increases.

20. The robot arm apparatus according to claim 19, wherein the processing circuitry raises the viscosity of driving of the joint unit as the enlargement factor increases.

21. The robot arm apparatus according to claim 19, wherein the processing circuitry selects a characteristic from a plurality of characteristics prescribing a relationship between the enlargement factor and the viscosity of driving of the joint unit, and controls the viscosity of driving of the joint unit based on the selected characteristic.

22. The robot arm apparatus according to claim 19, wherein the robot arm apparatus is an apparatus for medical use.

23. The robot arm apparatus according to claim 19, wherein the state of the joint unit is an orientation of the multi-link structure.

24. The robot arm apparatus according to claim 19, wherein the state of the joint unit is a driving velocity of the joint unit.

25. The robot arm apparatus according to claim 19, wherein the state of the joint unit is a driving direction of the joint unit.

* * * * *